United States Patent [19]

Fritch et al.

[11] Patent Number: 5,155,273

[45] Date of Patent: * Oct. 13, 1992

[54] PRODUCTION OF ACETAMINOPHEN

[75] Inventors: John R. Fritch, Corpus Christi, Tex.; O. Stanley Fruchey, Bad Soden/T.S., Fed. Rep. of Germany; Theodore Horlenko, Corpus Christi, Tex.; Daniel A. Aguilar, Corpus Christi, Tex.; Charles B. Hilton, Corpus Christi, Tex.; Phillip S. Snyder, Rock Hill, S.C.; William J. Seeliger, Corpus Christi, Tex.

[73] Assignee: Hoechst Celanese Corporation, Somerville, N.J.

[*] Notice: The portion of the term of this patent subsequent to Sep. 4, 2007 has been disclaimed.

[21] Appl. No.: 556,589

[22] Filed: Jul. 20, 1990

Related U.S. Application Data

[63] Continuation-in-part of Ser. No. 217,652, Jul. 12, 1988, Pat. No. 4,954,652.

[51] Int. Cl.$^5$ ............... C07C 231/05; C07C 233/42; C07C 235/12; C07C 235/16
[52] U.S. Cl. .................. 564/223; 564/305
[58] Field of Search ................. 564/223, 305

[56] References Cited

U.S. PATENT DOCUMENTS

| | | | |
|---|---|---|---|
| 4,524,217 | 6/1985 | Davenport et al. | 564/223 |
| 4,560,789 | 12/1985 | Davenport et al. | 560/142 |
| 4,568,763 | 2/1986 | Davenport et al. | 560/142 |
| 4,954,652 | 9/1990 | Fritch et al. | 564/223 |

FOREIGN PATENT DOCUMENTS 0168908 12/1988 European Pat. Off. .

Primary Examiner—Thurman K. Page
Assistant Examiner—Carlos Azpuru
Attorney, Agent, or Firm—D. R. Cassady

[57] ABSTRACT

N-acetyl-para-aminophenol is prepared by contacting 4-hydroxyacetophenone oxime with a Beckmann rearrangement catalyst in an alkyl alkanoate reaction solvent. An integrated process is disclosed wherein 4-hydroxyacetophenone is reacted with a hydroxylamine salt and a base to obtain 4-hydroxyacetophenone oxime, the oxime product is extracted from the resulting reaction mixture with a substantially water-immiscible solvent, and the mixture of oxime and substantially water-immiscible solvent is contacted with a Beckmann rearrangement catalyst to produce N-acetyl-para-aminophenol. Novel Beckamnn rearrangement catalysts are used to limit by-product formation in the ester solvent.

41 Claims, No Drawings

PRODUCTION OF ACETAMINOPHEN

This application is a Continuation-in-part of U.S. Ser. No. 217,652, filed Jul. 12, 1988 now U.S. Pat. No. 4,954,652.

This invention relates to a novel process for the production of N-acetyl-para-aminophenol (APAP) by the Beckmann rearrangement of 4-hydroxyacetophenone oxime using an acid catalyst. The invention is also concerned with an integrated process for preparing APAP by first producing 4-hydroxyacetophenone oxime from 4-hydroxyacetophenone (4-HAP), extracting the oxime from the reaction mixture with a solvent, and proceeding with the acid catalyzed Beckmann rearrangement of 4-hydroxyacetophenone oxime in the solvent used to extract the oxime.

BACKGROUND OF THE INVENTION

It is known to prepare N-acyl-hydroxyaromatic amines, e.g., N-acetyl-para-aminophenol (APAP), by acetylating the corresponding hydroxy aromatic amine, e.g. para-aminophenol, with an acetylating agent such as an anhydride, e.g., acetic anhydride. However, this reaction may cause problems such as the difficulty of mono-acetylating the amine group, oligomerization of the hydroxy aromatic amine, and color body formation. Nonetheless, the APAP made by this reaction is an important commodity of commerce, being one of the most widely used over-the-counter analgesics.

In U.S. Pat. No. 4,524,217 there is disclosed a novel process for the preparation of N-acyl-hydroxy aromatic amines, in general, and N-acetyl-para-aminophenol (APAP), in particular. The APAP is formed by a two-step process in which the first step involves reacting 4-hydroxyacetophenone (4-HAP) with a hydroxylamine salt and a base to obtain the ketoxime of the ketone (4-HAP oxime), and then subjecting the ketoxime to a Beckmann rearrangement in the presence of a catalyst to form APAP. Although various materials can be used as the Beckmann rearrangement catalyst, U.S. Pat. No. 4,524,217 discloses preferred use of thionyl chloride in liquid sulfur dioxide. The entire content of U.S. Pat. No. 4,524,217 is herein incorporated by reference.

Although sulfur dioxide has been found to be an excellent solvent for the Beckmann rearrangement of 4-HAP oxime to APAP or acetaminophen, there are certain characteristics of sulfur dioxide which are disadvantageous. For one, $SO_2$ is toxic. Accordingly, extraordinary precautions must be taken to handle and contain the sulfur dioxide and such precautions obviously require specialized equipment and procedures. For example, centrifuges do not adequately contain sulfur dioxide and therefore cannot be used for separation of the crude solid APAP product from the sulfur dioxide reaction liquor. Consequently, such separation must be accomplished by filtration with equipment that is more expensive to purchase and operate than a centrifuge. Furthermore, centrifugation is inherently suited for continuous processing, whereas filtration is not. Additionally, $SO_2$ is corrosive and requires expensive metallurgy. Use of $SO_2$ as solvent may also lead to the formation of metallic contaminants from the processing equipment. Such contaminants may affect reaction rates and/or lead to the formation of by-products. Obviously, since APAP is an analgesic for human consumption, the product should be as pure as possible, and, thus, minute impurities from corrosion products are definitely not desirable. Removal of corrosion products from the APAP adds to the operating costs. Moreover, the $SO_2$ must be pressurized for use in the liquid state as solvent. Pressurization, containment, and corrosion problems all require additional equipment and operating costs.

Another disadvantage with the prior two-step process of producing APAP from 4-HAP by first forming the 4-HAP oxime and then subjecting the oxime to Beckmann rearrangement with thionyl chloride in $SO_2$ is that the oxime is prepared in water and must be recovered by chilling the aqueous oximation product to crystallize the oxime. The crystallized oxime must then be collected from the aqueous oximation liquor, washed, and dried prior to Beckmann rearrangement. The dried oxime is then fed to the APAP reactor via a hopper system. This arrangement requires solids crystallization, collection, drying, storage, and handling and the consequent use of additional and expensive equipment.

Use of sulfur dioxide as the solvent for Beckmann rearrangement has yet further disadvantages. Before the crude APAP product can be neutralized and purified in aqueous media, substantially all of the sulfur dioxide solvent must be removed. Such removal requires filtration of sulfur dioxide from the crude solid APAP product, evaporation of most sulfur dioxide remaining on the crude solid APAP filter cake, and, finally, chemical neutralization of any sulfur dioxide still remaining on the crude solid APAP. Recovery of the sulfur dioxide evaporated or neutralized from the crude solid APAP is difficult and sometimes uneconomical. During subsequent purification, the crude solid APAP is dissolved off the filter with hot water. Substantially all traces of water must then be removed from the filter and its containment vessel before entry of the sulfur dioxide/APAP product slurry from the next batch. Sulfur dioxide recovered from the Beckmann reaction must remain substantially anhydrous to be suitable for use in subsequent Beckmann reactions. Removal of water from sulfur dioxide is difficult and/or impractical. The additional equipment and procedures needed to remove sulfur dioxide from the crude solid APAP product and to then remove water from the filter and its containment vessel add to both capital and operating costs.

Accordingly, it would be advantageous to provide an alternative solvent to $SO_2$ for use in the Beckmann rearrangement of 4-HAP oxime to APAP. Such a solvent should be less toxic, less volatile, and less corrosive than $SO_2$. The solvent must also provide good yields of APAP, preferably at least about 50% and more preferably at least about 60%. The solvent must also provide for the formation of a pure APAP product having a melting point range preferably between about 168° C. and about 172° C. (the USP specification) and having a dry-basis purity of preferably at least about 98% wt % (the USP specification) and more preferably at least about 99.9 wt %. As disclosed in copending aforementioned U.S. Ser. No. 217,652, ester solvents have been found useful in the Beckmann rearrangement of 4-HAP oxime to APAP and offer a viable alternative to $SO_2$ An important feature of the ester solvent is the ability of the ester solvent to extract the 4-HAP oxime from the reaction forming mixture. Accordingly, the oxime/solvent mixture can be directly contacted with the Beckmann rearrangement catalyst without separation and crystallization of the 4-HAP oxime.

The ester solvent is particularly useful not only because of its ability to extract the 4-HAP oxime but also since the ester solvent is substantially water-immiscible, forms a low-boiling azeotrope with water, can be dried easily by distillative removal of water, and can be removed from water easily by distillation to allow for substantially easier recovery and purification of the APAP product than is possible with SO$_2$ solvent.

It has been found, however, that the use of the ester solvent in the Beckmann rearrangement of 4-HAP oxime to APAP tends to lead to the formation of by-product N-methyl-p-hydroxybenzamide (MHBA). Accordingly, it would be useful to use the ester solvent for the Beckmann rearrangement of 4-HAP oxime to APAP and overcome the problem of by-product formation which has been found.

It is therefore the primary objective of the present invention to provide an alternative solvent to SO$_2$ in the above-described Beckmann rearrangement reaction, which solvent is less toxic, less volatile, and less corrosive; which reduces capital costs; and which can greatly reduce the handling and operating costs of the two-step process of forming APAP from 4-hydroxyacetophenone.

It is another object of this invention to provide for novel Beckmann rearrangement catalysts which are particularly effective in reducing by-product formation upon use of ester solvents for the reaction.

Still another object of this invention is to provide an effective and efficient method of separation and purification of APAP product formed by the Beckmann rearrangement of 4-HAP oxime in an ester solvent.

SUMMARY OF THE INVENTION

In accordance with the present invention, alkyl alkanoate esters are used as the solvent for the Beckmann rearrangement of 4-hydroxyacetophenone oxime (4-HAP oxime) to acetaminophen (APAP). The Beckmann rearrangement utilizes an appropriate acidic catalyst such as thionyl chloride or phosphorus oxytrichloride. Novel acidic Beckmann rearrangement catalysts which have a carbon atom as the active electrophilic site are particularly advantageous for substantially reducing or eliminating formation of the Beckmann rearrangement by-product N-methyl-p-hydroxybenzamide (MHBA) when the above esters are used as the reaction solvent. These novel acidic Beckmann rearrangement catalysts which have a carbon atom as the active electrophilic site include N-methylacetonitrilium tetrafluoroborate, trifluoroacetic anhydride, or the Vilsmeier reagent prepared from N,N-dimethylformamide (DMF) and thionyl chloride.

The Beckmann rearrangement may be carried out in the presence of potassium iodide, which serves to minimize the formation of by-products which contaminate the APAP product. Activated carbon may also be added to the mixture of 4-HAP oxime and ester solvent to help prevent retention of color in the APAP product.

An important advantage of utilizing alkyl alkanoate esters as the solvent for the Beckmann rearrangement of 4-HAP oxime to APAP is that the alkyl alkanoate esters can be utilized to extract the 4-HAP oxime from the aqueous product which is formed from the reaction of 4-HAP with hydroxylamine in the first step of the integrated process. After removal of water, preferably by azeotropic distillation, the extracted 4-HAP oxime and alkyl alkanoate ester mixture can be treated directly with an appropriate acidic catalyst to effect Beckmann rearrangement. Another advantage of utilizing alkyl alkanoate esters as the solvent for the Beckmann rearrangement of 4-HAP oxime to APAP is that aqueous media can be used to assist removal of such solvents from the crude solid APAP product.

DETAILED DESCRIPTION OF THE INVENTION

In accordance with this invention, N-acetyl-para-aminophenol (APAP) is produced by reacting 4-hydroxyacetophenone (4-HAP) with hydroxylamine to form the ketoxime of 4-HAP and subjecting the ketoxime to a Beckmann rearrangement in the presence of an alkyl alkanoate ester solvent and an appropriate acidic catalyst to form the N-acyl-hydroxyaromatic amine.

The ketoxime formation proceeds as in equation (I):

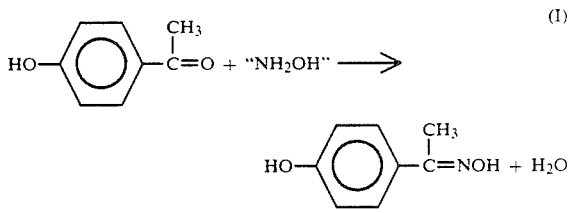

The Beckmann rearrangement to form the desired APAP product proceeds as in equation (II):

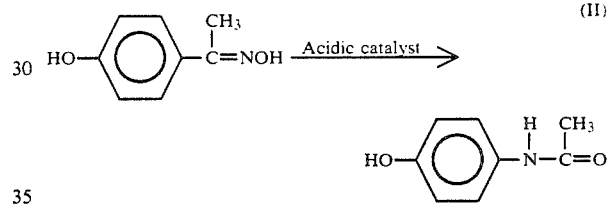

4-Hydroxyacetophenone used to form the oxime may be prepared by any method known in the art. For example, it may be prepared by the Fries rearrangement of phenyl acetate or, alternatively, in a Friedel-Crafts acetylation of phenol. The catalyst for both mentioned reactions is preferably hydrogen fluoride, but any other catalyst known in the art to be effective for the Fries or Friedel-Crafts reactions may be used, e.g., aluminum chloride, zinc chloride or boron trifluoride. A more detailed description of methods of forming the hydroxyaromatic ketone are described in the aforementioned U.S. Pat. No. 4,524,217.

The conversion of 4-HAP into the ketoxime by equation (I) is accomplished by contacting the ketone with a hydroxylamine salt, e.g., hydroxylamine hydrochloride, hydroxylamine sulfate, hydroxylamine bisulfate, or hydroxylamine phosphate, and a base, e.g. ammonium hydroxide (aqueous ammonia), potassium hydroxide, sodium hydroxide, or lithium hydroxide. Since hydroxylamine is sensitive and decomposes in its free form, it is commercially supplied as one of its acid salts. The free hydroxylamine is liberated upon treatment of the acid salt with the base. If sodium hydroxide or aqueous ammonia is used as the base to liberate hydroxylamine from its acidic sulfate salt, then such liberation also produces sodium or ammonium sulfate, respectively, as a by-product. In the integrated process for producing APAP from 4-HAP (disclosed in detail below) wherein Beckmann reaction solvent is used to extract 4-HAP oxime from the aqueous oximation mixture, it is preferred to use a strong base such as the alkali metal hydroxides to liberate the hydroxylamine.

The base should be used in an amount, for example, of 0.5 to 2 molar equivalents per molar equivalent of starting hydroxylamine. The base is preferably used in an amount of 0.8-1.0 molar equivalents per molar equivalent of starting hydroxylamine so that a small amount of hydroxylamine remains in the form of its acid salt to create a pH buffer that maintains the pH of the oximation reaction in the range of 3-7. Use of larger amounts of base can cause the pH to rise above 7 and results in initiating undesirable condensation reactions of 4-HAP and its oxime. The hydroxylamine acid salt is preferably used in an amount of 1-2 molar equivalents of starting hydroxylamine per mole of starting 4-HAP. Oximation is run at a temperature, for example of 0° to 200° C., for a period of from about 5 minutes to 4 hours. Any pressure may be used, e.g., 80 mm of mercury to 20 atmospheres absolute. The reaction is preferably carried out in an aqueous or alcoholic medium, i.e., in the presence of water and/or an alcohol such as methanol, ethanol, or isopropanol.

The 4-HAP oxime is converted into APAP by a Beckmann rearrangement as shown in equation (II) by contacting the ketoxime with an alkyl alkanoate ester solvent and an appropriate acidic catalyst at a reaction temperature, for example, of from 0° to 100° C. for a period of from about 5 minutes to 4 hours. The pressure is not critical and may be, for example, in the range of 1 mm of mercury to 10 atmospheres absolute. The Beckmann rearrangement can be carried out quite successfully with large amounts of undissolved 4-HAP oxime solids and large amounts of undissolved APAP solids suspended in the reaction mixture. The amount of reaction solvent should be sufficiently large so that any undissolved solids form a slurry that settles under the force of gravity and is stirable, but should not be so large as to prevent crystallization of the APAP product when the reaction mixture is chilled. Thus, the reaction solvent should be present in amounts of from about 0.75-50:1 by weight with respect to the 4-HAP oxime. The weight ratio of oxime to Beckmann rearrangement catalyst ranges from about 5:1 up to about 300:1.

The Beckmann reaction is carried out to 4-HAP oxime conversions of preferably at least about 50% and more preferably at least about 80% to minimize losses of unreacted 4-HAP oxime to recrystallization and wash liquors. Conversions of 4-HAP oxime during Beckmann rearrangements can be controlled by use of an appropriate quantity of catalyst. A certain quantity of catalyst gives substantially 100% 4-HAP oxime conversion; with smaller amounts of catalyst, 4-HAP oxime conversions decrease with decreasing catalyst quantity.

The process of this invention is preferably carried out by adding an alkali metal iodide such as potassium iodide to the 4-hydroxyacetophenone oxime prior to carrying out the Beckmann rearrangement in alkyl alkanoate ester solvent. Potassium iodide serves to minimize formation of by-products that can contaminate the APAP product. The amount of alkali metal iodide utilized is extremely small and very acceptable results have been obtained when using 0.2 wt% of potassium iodide relative to the oxime. It should be realized that no particular advantage is gained in going over the 0.2 gram KI per 100 grams of 4-hydroxyacetophenone oxime but, obviously, such can be done if desired. The amount of inorganic iodide which should be added is that amount sufficient to substantially prevent the formation of chlorinated by-products and said amount is usually in the range varying from about 0.02 gram to about 2.0 grams of potassium iodide per 100 grams of 4-hydroxyacetophenone oxime which is subjected to the Beckmann rearrangement.

The manner in which iodide is added to the Beckmann rearrangement reactor is by no means critical. Iodide can be added directly to the reactor or can be contained in a recycle stream of the reaction mixture solvent. A more detailed description of potassium iodide addition to the Beckmann rearrangement reactor is given in commonly assigned, U.S. Pat. No. 4,855,499, the entire content of which is herein incorporated by reference.

Activated carbon may also be added to the Beckmann rearrangement reaction mixture in a manner to be described later in more detail.

Appropriate acidic catalysts for use in the Beckmann rearrangement of 4-hydroxyacetophenone oxime to APAP include, but are not limited to, thionyl chloride; methanesulfonyl chloride; trifluoromethanesulfonyl chloride; methanesulfonic anhydride; the mixed anhydride of trichloroacetic and methanesulfonic acids; p-toluenesulfonic anhydride; phosphorus oxytrichloride; phosphorus pentoxide; phenylphosphonic dichloride; diphenylphosphinic chloride; trifluoroacetic anhydride; trichloroacetic anhydride; trifluoroacetyl chloride; trichloroacetyl chloride; oxalyl chloride; ethyl oxalyl chloride; phosgene; trichloromethyl chloroformate (diphosgene); methyl chloroformate; N,N-dimethylcarbamyl chloride; nitrilium salts of the formula $(R'C\equiv N^+R'')X^-$, where R' and R'' can each independently be alkyl such as methyl, isopropyl or substituted alkyl, aryl, or substituted aryl and where $X^-$ can be $BF_4^-$, $SbF_6^-$, $PF_6^-$, $FeCl_4^-$, $AlCl_4^-$, $Cl^-$, $Br^-$, or $I^-$; and any Vilsmeier reagent prepared from a carboxylic acid amide (such as N,N-dimethylformamide (DMF), N,N-dimethylacetamide (DMA), or N-methylpyrrolidinone (NMP)) and a reagent capable of replacing oxygen with halogen (such as thionyl chloride, phosphorus oxytrichloride, phosphorus pentachloride, trichloroacetyl chloride, trichloromethyl chloroformate (diphosgene), or phosgene). For the purposes of the present specification and claims, the term "catalyst" includes any material capable of initiating Beckmann rearrangement of 4-HAP oxime to APAP. The Beckmann rearrangement might be described formally as the chain-reaction process depicted in the following equation (III):

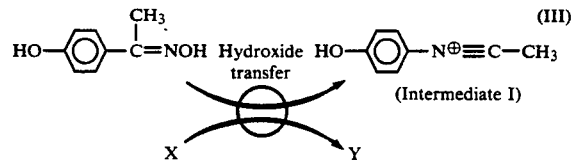

In equation (III), 4-HAP oxime is converted to chain intermediate I with simultaneous conversion of species X to species Y. Examples of species X and corresponding species Y are shown in the following table:

| X | Y |
|---|---|
| SOCl₂ | SO₂ + HCl + Cl⁻ |
| ⅓POCl₃ | ⅓H₃PO₄ + Cl⁻ |
| (CH₃)₂N⁺=CHCl | (CH₃)₂NCH=O + HCl |
| (CF₃CO)₂O | CF₃CO₂H + CF₃CO₂⁻ |

-continued

| X | Y |
|---|---|
| $CH_3C\equiv N^+-CH_3$ | $CH_3C=O$<br>$\quad\backslash NHCH_3$ |
| Intermediate I | APAP |

The first five entries for species X in the above table, respectively thionyl chloride, phosphorus oxytrichloride, Vilsmeier reagent N,N-dimethylchloroforminium cation, trifluoroacetic anhydride, and N-methylacetonitrilium cation, are herein nominally referred to as Beckmann rearrangement "catalysts." Assuming the role of species X in the above equation (III), such "catalysts" initiate the Beckmann rearrangement by converting 4-HAP oxime to chain intermediate I. Chain intermediate I (as species X) is then converted to APAP (as species Y) with simultaneous regeneration of chain intermediate I from 4-HAP oxime.

The active electrophilic site of a Beckmann rearrangement catalyst is the atom of the catalyst at which the catalyst reacts with an oxime. With catalysts such as thionyl chloride or phosphorus oxytrichloride that have a sulfur atom or a phosphorus atom as the active electrophilic site, it has been found that Beckmann rearrangement of 4-HAP oxime in ester solvents produces small amounts of N-methyl-p-hydroxybenzamide (MHBA) by-product. The MHBA by-product is only partially removed from the desired APAP product by conventional purification techniques such as aqueous recrystallization.

In comparison to catalysts that have a sulfur or phosphorus atom as the active electrophilic site, Beckmann catalysts having a carbon atom as the active electrophilic site can offer the advantage of producing substantially less MHBA by-product during Beckmann rearrangement of 4-HAP oxime to APAP in ester solvents. For example, no MHBA by-product is formed during Beckmann rearrangement of 4-HAP oxime to APAP in ester solvents with catalysts such as trifluoroacetic anhydride, trichloroacetic anhydride, or N-methylacetonitrilium tetrafluoroborate, all of which have a carbon atom as the active electrophilic site and none of which produces HCl or Cl$^-$ as a by-product.

Catalysts that have a carbon atom as the active electrophilic site but that produce HCl or Cl$^-$ on reaction with 4-HAP oxime include trifluoroacetyl chloride, trichloroacetyl chloride, oxalyl chloride, ethyl oxalyl chloride, phosgene, trichloromethyl chloroformate (diphosgene), methyl chloroformate, N,N-dimethylcarbamyl chloride, and any Vilsmeier reagent prepared from a carboxylic acid amide (such as N,N-dimethylformamide (DMF), N,N-dimethylacetamide (DMA), or N-methylpyrrolidinone (NMP)) and a reagent capable of replacing oxygen with halogen (such as thionyl chloride, phosphorus oxytrichloride, phosphorus pentachloride, trichloroacetyl chloride, trichloromethyl chloroformate (diphosgene), or phosgene). Such catalysts, in comparison to catalysts that have a sulfur or phosphorus atom as the active electrophilic site, still can offer the advantage of producing substantially less MHBA by-product during Beckmann rearrangement of 4-HAP oxime to APAP in ester solvents. The advantage is particularly found when the Beckmann rearrangement is run to a 4-HAP oxime conversion of no more than about 95% or when an appropriate base is incorporated with the catalyst or the Beckmann reaction mixture.

Bases capable of reducing the amount of MHBA produced during the Beckmann reaction include tertiary amines (such as pyridine or trialkylamine, e.g., triethylamine), carboxylic acid salts (such as sodium acetate or sodium trifluoroacetate), phosphate salts (such as ammonium dihydrogen phosphate), sodium metabisulfite, or surfactant salts (such as sodium dodecyl sulfate). Such bases presumably serve to scavenge HCl without destroying catalyst activity.

In the absence of such a base, MHBA formation accelerates with increasing 4-HAP oxime conversion and accelerates sharply at 4-HAP oxime conversions above about 95% with catalysts that have a carbon atom as the active electrophilic site but that produce HCl or Cl$^-$ on reaction with 4-HAP oxime. With such catalysts, it is therefore preferable to use an appropriate base or to limit 4-HAP oxime conversion to about 95% or less by use of an appropriate quantity of catalyst.

Use of bases (that presumably scavenge HCl without destroying catalyst activity) also can reduce the amount of MHBA produced in thionyl chloride-catalyzed Beckmann rearrangement of 4-HAP oxime to APAP in ester solvents.

The reaction solvent used in this invention is, as previously discussed, preferably an alkyl ester of an alkanoic acid. Preferably the alkylester group has 1 to 6 carbon atoms and the alkanoic acid contains 2 to 6 carbon atoms. Specific nonlimiting examples of alkyl alkanoate esters that have proven useful in the present invention include ethyl acetate, n-butyl acetate, methyl n-hexanoate, and n-hexyl acetate. A preferred solvent is made from alkyl esters of acetic acid. Acetate esters have the advantage of rendering degenerate any possible alkanoate exchange between the alkyl alkanoate ester and the N-acetyl-p-aminophenol product.

The use of alkyl alkanoate esters as the Beckmann rearrangement solvent is advantageous inasmuch as the Beckmann rearrangement can be carried out continuously or batchwise with a centrifuge rather than batchwise with a Nutsche (e.g. Rosemund) filter which is required utilizing SO$_2$ as the solvent. Alkyl alkanoate esters are much less volatile, less toxic, and less corrosive than sulfur dioxide and therefore avoid the previously described disadvantages of sulfur dioxide. Another important advantage of utilizing an alkyl alkanoate ester as the solvent is that the crystallization, isolation, drying, transport, handling, and storage of solid 4-HAP oxime can be eliminated by extracting 4-HAP oxime directly from the oximation product stream with the alkyl alkanoate ester, removing water from the resulting alkyl alkanoate ester solution of oxime, and adding an appropriate Beckmann rearrangement catalyst to the resulting dry mixture of oxime and alkyl alkanoate ester.

Although extraction of 4-HAP oxime with an alkyl alkanoate ester extraction solvent is preferably carried out on hot oximation product to prevent crystallization of 4-HAP oxime and to avoid the expense of a cooling step, the extraction can also be carried out on a chilled aqueous oximation product in which the 4-HAP oxime product has crystallized. In either case, mixing of the alkyl alkanoate ester extraction solvent with the aqueous oximation product yields two liquid phases: an upper liquid organic phase comprising the alkyl alkanoate ester and 4-HAP oxime, and a lower aqueous phase comprising water and the salt which is formed during liberation of the hydroxylamine. The weight ratio of extraction solvent to 4-HAP oxime product is preferably about 0.5-25:1 and is more preferably about 0.5-5:1. The aqueous phase thus obtained may be extracted with the alkyl alkanoate ester extraction solvent one or more times to recover additional 4-HAP oxime. Alternatively, the extraction of aqueous oximation product with alkyl alkanoate ester extraction solvent may be carried out continuously in a York-Scheibel countercurrent-type extractor.

The upper liquid organic phases are dried, preferably by distillative removal of water as a low-boiling azeotrope with the alkyl alkanoate ester extraction solvent. The alkyl alkanoate ester extraction solvent is preferably substantially immiscible with water. Under this circumstance, most of the water and most of the ester distilled from the 4-HAP oxime mixture will separate into different liquid phases. The distillate ester phase can be decanted off the distillate aqueous phase and recycled to the mixture of 4-HAP oxime and ester during the distillative removal of water. Most of the water present in the mixture of ester and 4-HAP oxime prior to distillation can be removed as a separate, relatively pure aqueous phase of the distillate. The distillation residue, which comprises a substantially dry mixture of 4-HAP oxime and alkyl alkanoate ester extraction solvent, can then be treated directly with an appropriate acidic catalyst to effect Beckmann rearrangement to APAP.

If the oxime is to be extracted with an alkyl alkanoate ester, it has been found that the use of a strong base such as sodium hydroxide has an important advantage over relatively weak bases such as ammonium hydroxide (aqueous ammonia) in the first stage of the process wherein is provided the liberation of free hydroxylamine from a corresponding acid salt such as hydroxylammonium sulfate. The disadvantage of weak bases such as ammonium hydroxide is that their use causes rearrangement of 4-HAP oxime to acetaminophen and hydrolysis of acetaminophen and 4-HAP oxime to p-aminophenol and 4-HAP, respectively, during the distillative drying of the extracted oxime. Traces of the acid salt corresponding to the weak base, for example, ammonium sulfate, presumably catalyze these undesirable side reactions during the distillative drying step. Furthermore, previously useful purification techniques failed to give an acceptable acetaminophen product when a relatively weak base such as ammonium hydroxide was used to liberate free hydroxylamine. Use of strong bases such as sodium hydroxide avoids the undesirable side reactions and permits successful purification of the crude acetaminophen product by previously disclosed methods. The by-products produced with a strong base, for example, sodium sulfate and water from sodium hydroxide, apparently do not catalyze undesirable reactions during the distillative drying step.

Addition of activated carbon to the mixture of 4-HAP oxime and ester solvent has been found to prevent substantial amounts of color from being retained in the APAP product from subsequent Beckmann rearrangement. The activated carbon is preferably added before addition of the Beckmann rearrangement catalyst. If the mixture of 4-HAP oxime and ester solvent is dried by azeotropic distillation, the activated carbon is preferably added before or during the azeotropic distillation. The activated carbon is preferably removed from the APAP product by dissolving the APAP product in hot water, filtering the activated carbon off the resulting aqueous solution of APAP, and cooling the aqueous filtrate to recrystallize the APAP product. Prevention of color retention in the APAP product by such use of activated carbon is particularly significant when ester Beckmann reaction filtrates are recycled. Such use of activated carbon prevents retention of color that cannot be removed by other means after the Beckmann reaction.

In preferred embodiments, the acetaminophen product is purified by neutralization with aqueous base and recrystallization from an aqueous medium. The ester solvent is removed from the acetaminophen product prior to recrystallization in the aqueous medium. The ester solvent can be removed from the acetaminophen by any of several methods, including, individually or in combination, filtration, washing filtered acetaminophen product with water, evaporation of solvent to a solid residue, and water-assisted distillative removal of ester.

Filtration of ester Beckmann reaction mixtures yields a filter cake of solid acetaminophen and an ester filtrate liquor that can be recycled to a subsequent Beckmann reaction. The filter cake of solid acetaminophen contains residual ester solvent that is preferably removed prior to recrystallization of the acetaminophen from an aqueous medium. The residual ester in the filter cake can be removed by evaporation and then recovered by condensation. However, substantially complete evaporation and recovery of residual ester solvent can consume considerable time and utilities such as vacuum, steam, cooling water, etc. The substantially ester-free filter cake can then be neutralized in an aqueous slurry with aqueous base.

Alternatively, residual ester Beckmann liquor can be washed from the APAP filter cake with an aqueous medium such as the mother liquor from a recrystallization of a previous batch of APAP or, preferably, the aqueous phase resulting from extraction of a crude oximation product with alkyl alkanoate ester solvent. Such washing dislodges the residual ester from the solid APAP by mechanical entrainment. The resulting wash liquors, on standing, separate into two phases, one of which (usually the top phase) is residual ester that can be separated and recovered. The other phase (usually the lower one) is an aqueous medium that can be used for further or other APAP filter cake washing operations. Use of the aqueous phase resulting from extraction of a crude oximation product is preferred in such APAP filter cake washing because this aqueous phase's high content of dissolved salts reduces the solubilities of ester and acetaminophen in the aqueous phase and the solubilities of water and acetaminophen in the ester phase.

With this aqueous washing procedure, neutralization can be carried out with aqueous base either before or after filtration of the Beckmann reaction mixture. The neutralization is preferably carried out with the same aqueous medium that is used to wash the acetaminophen filter cake. If neutralization is carried out before filtration, the aqueous medium and the aqueous base are preferably mixed with the crude Beckmann reaction slurry inside the Beckmann reactor. The resulting neutralized slurry can then be filtered in its entirety to provide a filter cake of neutralized acetaminophen still containing some residual ester. Conducting neutralization before filtration has the advantage of reducing the metallurgical requirements (and cost) of the filter. If neutralization is carried out after filtration, the acetaminophen filter cake is slurried in an aqueous medium, aqueous base is added, and the resulting neutralized slurry is filtered.

If neutralization is carried out before residual ester is washed off the acetaminophen filter cake, the residual ester can be recovered by allowing the neutralization liquor filtrate to separate into an ester phase and an aqueous phase, the latter of which can be used for further or other acetaminophen filter cake washing operations.

As an alternative to or in conjunction with the evaporation or washing procedures just described, the acetaminophen filter cake can be slurried in an aqueous medium to assist distillative removal of residual ester. As yet another alternative, filtration of the ester Beckmann reaction mixture can be avoided completely, permitting conversion of 4-HAP to recrystallized acetaminophen in a single vessel, by addition of an aqueous medium to the ester Beckmann reaction mixture to assist distillative removal of ester solvent. The ester solvent employed for the Beckmann reaction preferably forms a low-boiling azeotrope with water. Distillation of the mixture of acetaminophen, aqueous medium, and ester removes the ester from a residual aqueous mixture of acetaminophen. The aqueous medium used to assist distillative removal of ester is preferably the same as that used for neutralization, is preferably the same as that used for recrystallization, and is preferably the same as that used for neutralization and recrystallization.

As a means for removal of the last portions of ester solvent from acetaminophen product, water-assisted distillation is preferred to evaporation in the absence of water. Water-assisted distillative removal offers more efficient mixing and heat transfer, and, for reasons including these, can be carried out at lower temperatures, in less time, and with less consumption of utilities. These advantages are particularly great when distillative removal of ester is assisted with water vapor (i.e, steam) passed directly into the acetaminophen/ester mixture. The ability to remove ester at lower temperatures avoids formation of undesirable by-products and impurities.

However, distillative removal of the first portions of ester solvent from acetaminophen product might preferably be done in the absence of water to avoid losses of heat to vaporization of water. Distillative removal of ester solvent permits elimination of filtration, elimination of ester Beckmann reaction liquor recycle, and elimination of the resulting build-up of colored impurities.

Subsequent to the recovery of the product of the Beckmann rearrangement, the ester solvent can be recycled to either the Beckmann rearrangement or to the oxime extraction.

The invention will be further illustrated by the following nonlimiting examples.

EXAMPLE 1

A slurry of 4-HAP oxime (100.00 g, 0.6617 mols) and potassium iodide (0.200 g) in ethyl acetate (185 mL) was stirred and heated to 50° C. under nitrogen (290 torr absolute total pressure). A solution of thionyl chloride (1.0 mL, 1.631 g, 13.71 mmole) in ethyl acetate (15 mL) was then added over 25 minutes to the stirred 4-HAP oxime/ethyl acetate slurry. The temperature of the reaction mixture was maintained at 50°-51° C. by allowing the heat of reaction to reflux the ethyl acetate solvent under 290 torr absolute total pressure. Within about ten minutes after the start of the thionyl chloride addition, the reaction mixture was a nearly homogeneous, light amber liquid. White solid APAP then began to precipitate. The refluxing started to subside after about 90% of the thionyl chloride had been added. After the thionyl chloride addition was completed, the reaction mixture was allowed to cool to 40° C. over about ten minutes and was then chilled in an ice bath to 3° C. The reaction slurry was filtered under nitrogen to give a cake of light yellow Beckmann reaction solids and a filtrate of yellow Beckmann reaction liquor. Residual ethyl acetate was pumped off the reaction solids at 0.025 torr and ambient temperature. The dried reaction solids were then purified by known washing, filtering and recrystallization procedures. Results are shown in Table 1. The solid filter material used in the purification was dried under vacuum (0.025 torr) at ambient temperature to a mass 3.53 g greater than the weight of the starting filter material; this mass increase presumably was due mostly to adsorbed APAP. Throughout the entire preparation, the crude APAP solids and purified APAP solids were granular, free of tackiness, and easily handled.

EXAMPLE 2

The preparation of Example 1 was repeated with the starting 4-HAP oxime/ethyl acetate slurry containing 90 mL instead of 185 mL of ethyl acetate. Under these conditions, the reaction mixture contained substantial amounts of white solid throughout the entire reaction period. As the refluxing subsided near completion of the thionyl chloride addition, the reaction slurry became so viscous that it no longer settled under the force of gravity. Throughout the entire preparation, the crude APAP solids and purified APAP solids were granular, free of tackiness, and easily handled. Results are shown in Table 1.

EXAMPLE 3

The preparation of Example 1 was repeated with the starting 4-HAP oxime/ethyl acetate slurry containing 475 mL instead of 185 mL of ethyl acetate. This volume of ethyl acetate was sufficient to dissolve essentially all of the starting 4-HAP oxime at 25° C. The reaction mixture remained essentially homogeneous until about one-third of the thionyl chloride catalyst had been added, at which time the APAP product started to precipitate as a white solid. Throughout the entire preparation, the crude APAP solids and purified APAP solids were granular, free of tackiness, and easily handled. Results are shown in Table .

EXAMPLE 4

The preparation of Example 1 was repeated without KI. The crude and purified APAP products were noticeably more colored than their counterparts from Example 1. Throughout the entire preparation, the crude APAP solids and purified APAP solids were granular, free of tackiness, and easily handled. Results are shown in Table 1.

EXAMPLE 5

The preparation of Example 1 was repeated with the Beckmann reaction being run at 32 ° C. under 150 torr absolute total pressure. Throughout the entire preparation, the crude APAP solids and purified APAP solids were granular, free of tackiness and easily handled. Results are shown in Table 1.

EXAMPLE 6

The preparation of Example 1 was repeated with the following modifications. In the starting 4-HAP oxime/ethyl acetate slurry, the ethyl acetate Beckmann reaction liquor from the preparation of Example 1 was used in place of 185 mL of fresh ethyl acetate. The catalyst solution consisted of thionyl chloride (1.3 mL instead of 1.0 mL) in fresh ethyl acetate (50 mL instead of 15 mL to make up the ethyl acetate loss in the drying step of Example 1). Fresh, acid-washed activated carbon (0.500 g) was now also included with the starting 4-HAP oxime/ethyl acetate slurry. The dried reaction solids were purified by known methods. Throughout the entire preparation, the crude APAP solids and purified APAP solids were granular, free of tackiness, and easily handled. Results are shown in Table 1.

EXAMPLE 7

To a stirred solution of 4-HAP (100.00 g) and hydroxylamine sulfate (63.6 g) in water (370 mL) heated to 80° C. was added a solution of sodium hydroxide (30.5 g) in water (100 mL) over five minutes. The stirred, homogeneous, yellow reaction mixture was refluxed at 102°-103° C. under air for 20 minutes and then cooled to 25° C. Ethyl acetate (200 mL) was then added to the cooled reaction mixture, which contained a large amount of crystallized 4-HAP oxime. The three-phase mixture was shaken well for about half a minute and then allowed to settle. Two liquid phases separated completely within about one minute, leaving only a small amount of undissolved solid. The bottom aqueous phase and the undissolved solids were separated from the upper ethyl acetate phase and then extracted with two more 100 mL portions of ethyl acetate.

The three ethyl acetate extracts were combined and dried by azeotropic distillation under nitrogen at atmospheric pressure in two steps. The first step, which employed a Dean-Stark trap under conditions of total reflux, removed 34.5 mL of aqueous phase distillate. The second step, which employed a 10-tray Oldershaw column and a reflux to takeoff ratio of 3:1, yielded 200 mL of cloudy distillate and a stable final overhead temperature of 77.1° C. The distillates were found by analysis to contain less than 0.02 wt % each of acetic acid and ethanol.

On cooling, 4-HAP oxime crystallized from the amber distillation residue. The resulting dry slurry of 4-HAP oxime in ethyl acetate was then subjected to the conditions of the Beckmann rearrangement described in Example 1 using 0.200 g of KI, 85 mL of fresh additional ethyl acetate, and a catalyst solution of thionyl chloride (1.3 mL) in ethyl acetate (15 mL). Throughout the entire preparation, the crude APAP solids and purified APAP solids were granular, free of tackiness, and easily handled. Results are shown in Table 1.

EXAMPLE 8

The oximation/Beckmann reaction sequence of Example 7 was repeated with only one significant modification now described. The aqueous reaction mixture from the oximation reaction was drained hot (about 100° C.) over five minutes into a round bottom flask containing ethyl acetate (200 mL) and equipped with a reflux condenser. The ethyl acetate refluxed very gently under atmospheric pressure for only a short period during the addition. When the addition was complete, the mixture was at about 73° C. and was mixed well by stirring vigorously for about one minute. Two homogeneous liquid phases then separated completely within about one minute, leaving no undissolved solids. The lower (aqueous) phase was extracted with two more 100 mL portions of ethyl acetate as described in Example 7.

The distillates from the azeotropic drying steps were found by analysis to contain less than 0.02 wt % each of ethanol and acetic acid. Throughout the entire preparation, the crude APAP solids and purified APAP solids were granular, free of tackiness, and easily handled. Results are shown in Table 1.

EXAMPLE 9

The oximation/Beckmann rearrangement reaction sequence of Example 7 was repeated with 29 wt % aqueous ammonia (60 mL) being used instead of aqueous sodium hydroxide as the base to liberate free hydroxylamine during the oximation. Results are shown in Table 1.

EXAMPLE 10

The oximation/Beckmann rearrangement sequence of Example 8 was repeated with the following modifications. Instead of 370 mL of fresh water, the oximation used 148 mL of fresh water and 222 mL of the aqueous phase remaining after extraction of the oximation product of Example 8 with ethyl acetate. Instead of being drained into 200 mL of fresh ethyl acetate, the hot oximation product was drained into the ethyl acetate Beckmann reaction liquor recovered from the preparation of Example 8. Extraction of the oximation product was then completed with two 100 mL portions of the wet ethyl acetate distilled off the ethyl acetate extracts of Example 8. For the Beckmann rearrangement, the ethyl acetate solution of thionyl chloride used 50 mL of fresh ethyl acetate instead of 15 mL to make up the ethyl acetate loss in the drying step of Example 8. Fresh, acid-washed activated carbon (0.50 g) was now also included with the starting 4-HAP oxime/ethyl acetate slurry. After removal of residual ethyl acetate, the dried reaction solids were purified by known methods.

The distillates from the azeotropic drying steps were found by analysis to contain no more than 0.032 wt % each of ethanol and acetic acid. Throughout the entire preparation, the crude APAP solids and purified APAP solids were granular, free of tackiness, and easily handled. Results are shown in Table 1.

EXAMPLE 11

A slurry of 4-HAP oxime (100.00 g, 0.6617 moles) in n-hexyl acetate (450 mL) containing no potassium iodide was stirred and heated to 60° C. under nitrogen (8 torr absolute total pressure). A solution of thionyl chloride (1.3 mL, 2.120 grams, 17.82 mmole) in n-hexyl acetate (50 mL) was then added over 30 minutes to the stirred 4-HAP oxime/n-hexyl acetate slurry. The temperature of the reaction mixture was maintained at 58°-65° C. by allowing the heat of reaction to reflux the hexyl acetate solvent under 8 torr absolute total pressure. Within about five minutes after the start of the thionyl chloride addition, the reaction mixture was a nearly homogeneous amber liquid. Pale yellow solid APAP then precipitated during the remainder of the thionyl chloride addition. The refluxing started to subside after about 90% of the thionyl chloride had been added. After the thionyl chloride addition was completed, the reaction mixture was chilled in an ice bath to 5° C. The reaction slurry was filtered under nitrogen to give a cake of golden yellow Beckmann reaction solids and a filtrate of yellow Beckmann reaction liquor. Residual n-hexyl acetate was pumped off the reaction solids at 0.025 torr and ambient temperature. The dried reaction solids were then purified by known washing, filtration, and recrystallization procedures. The results shown in Table 1 do not include 2.85 g of 98.8% pure APAP that precipitated from the yellow Beckmann reaction liquor on standing overnight at room temperature under air. Throughout the entire preparation, the crude APAP solids and purified APAP solids were granular and handled without problem.

EXAMPLE 12

The preparation of Example 11 was repeated at 50° C. and 17 torr total absolute pressure with methyl n-hexanoate instead of n-hexyl acetate as the reaction solvent. Throughout the entire preparation, the crude APAP solids and purified APAP solids were granular and handled without problem. Results are shown in Table 1.

EXAMPLES 13-112

Examples 13-112 describe Beckmann rearrangement of 4-HAP oxime to APAP with a variety of catalysts, some of which produce little or no MHBA. Specific conditions and results for Examples 13-112 are shown in Tables 2-11. The following general procedure was used for Examples 13-112. The indicated amounts of the indicated catalyst components were mixed with typically 20-25 mL of ethyl acetate at room temperature. The resulting catalyst mixtures were added at room temperature from an addition funnel to a stirred slurry of 4-HAP oxime (about 100 g), potassium iodide (about 0.2 g), the indicated amounts of the indicated additives, and ethyl acetate (about 200 mL) heated to reflux at about the indicated temperature inside a nitrogen-purged reaction vessel. The indicated temperatures were achieved by adjustment of the reaction vessel's pressure, which was typically maintained at less than one atmosphere absolute. The reaction vessel was equipped with a 9° C. water-cooled condenser to reflux the ethyl acetate vapors. The catalyst mixtures were added (typically over 15-30 minutes) at a rate sufficient to maintain ethyl acetate reflux within the capacity of the condenser. The indicated reaction temperature was maintained for the indicated reaction time either with the heat of the Beckmann rearrangement or, if this was insufficient, with heat applied to the exterior bottom surface of the reaction vessel. The reaction mixtures were cooled to 0°-25° C. under nitrogen and then filtered. The oxime conversions, oxime accountabilities, and APAP and MHBA efficiencies and yields shown in Tables 2-11 are all based on both analyses of the ethyl acetate filtrates and analyses of the filtered solids.

In Example 19, 0.50 g of KI was used instead of 0.20 g.

In Example 25, the catalyst mixture was prepared by dropwise addition of the $SO_3$ to a stirred, 0° C. solution of the methanesulfonic acid in ethyl acetate (20 mL).

In Example 29, the reaction was carried out on half the scale indicated above and in Table 3. A slurry of potassium 4-HAP oxime-O-sulfonate (2.3 g) in ethyl acetate (60 mL) was added as catalyst over 7 minutes to a 48° C. slurry of 4-HAP oxime (50.0 g), KI (0.'g), sulfuric acid (1.50 g), and ethyl acetate (100 mL). The reaction mixture was then heated to 70° C. and stirred at this temperature for 102 minutes before being allowed to cool to room temperature.

In Examples 37 and 40, n-butyl acetate was used instead of ethyl acetate throughout, no potassium iodide was used, and the reactions were carried out on twice the scale indicated above and in Tables 4 and 5. In Example 37, neat $B_3.Et_2O$ catalyst was added to the oxime slurry without dilution. Examples 40 and 122 are in fact identical, and the procedure for these Examples is detailed below for Example 122. The procedure for recovery of recrystallized APAP product in Example 37 was the same as that for Example 122 below.

In Examples 26, 29, 37, and 38, the entire catalyst mixture was added to an about 50° C. 4-HAP oxime slurry over 7-45 minutes before the Beckmann reaction temperature was increased to the indicated level.

In Example 39, the $((AcO)_2B)_2O$ catalyst was incorporated with the original mixture of 4-HAP oxime and ethyl acetate in the reaction vessel before heating.

In Examples 45 and 46, the catalyst mixture was stirred and maintained at about 0°-4° C. throughout its entire preparation and until its use as Beckmann rearrangement catalyst. A solution of the indicated amount of $CCl_3COCl$ in ethyl acetate (7 mL in Example 45 and 15 mL in Example 46) was added over 20 minutes (Example 45) or 30 minutes (Example 46) to a stirred solution of the indicated amount of 4-HAP oxime in ethyl acetate (20 mL in Example 45 and 35 mL in Example 46). In Example 45, an additional 10 mL of 0°-4° C. ethyl acetate was added to the catalyst mixture midway into the $CCl_3COCl$ addition. After completion of the $CCl_3COCl$ addition, the resulting mixture was stirred for about 10 minutes before dropwise addition of the indicated amount of triethylamine (neat in Example 45 and as a solution in 5 mL of ethyl acetate in Example 46) over about 10 minutes. The resulting mixture was then stirred for about 2 hours before use as Beckmann rearrangement catalyst. The catalyst mixture is believed to have contained 4-HAP oxime-O-trichloroacetate as the active species. In Example 45, 100.0 g of 4-HAP oxime slurried in 190 mL of ethyl acetate was used for Beckmann rearrangement. In Example 46, 94.7 g of 4-HAP oxime slurried in 165 mL of ethyl acetate was used for Beckmann rearrangement.

In Example 47, the catalyst mixture was stirred overnight at room temperature prior to use as the Beckmann rearrangement catalyst.

In Example 48, the triethylamine (3.5 g) was added dropwise over 5 minutes to a stirred solution of the trifluoroacetic acid (4.0 g) in 50 mL of the ethyl acetate before addition of the remaining ethyl acetate (150 mL) and the 4-HAP oxime (100.0 g).

In Examples 61-67, 70-83, and 87-98, the indicated catalyst components were combined about 30 minutes prior to use as the Beckmann rearrangement catalyst. While standing at room temperature with agitation about once every ten minutes during this approximately 30 minute period, the indicated components of the catalyst mixture are believed to have reacted to produce Vilsmeier reagents. Vilsmeier reagents are also believed to have been produced in the catalyst mixtures for Examples 84-86, which were stirred at room temperature for about 18 hours before use as Beckmann catalysts. In Example 66, the catalyst mixture was prepared with 20 mL of tetrahydrofuran in addition to 20 mL of ethyl acetate. Formation of the Vilsmeier reagent from dimethylformamide and thionyl chloride in Examples 61-67 was indicated by its precipitation as colorless crystals. Most of these crystals were added from the addition funnel to the Beckmann reaction mixture as a suspension in the original catalyst mixtures. Most of the crystals remaining in the addition funnel were then added to the Beckmann reaction mixture after resuspension in an additional about 15 mL of ethyl acetate. The other Vilsmeier reagents did not precipitate.

In Example 82, 93.2 g of 4-HAP oxime was charged to the reaction vessel. The methanesulfonic acid and the sodium salt of 4-HAP oxime are believed to have reacted to produce sodium methanesulfonate and additional 4-HAP oxime in situ.

EXAMPLES 113–118

In Examples 113–118, oximation and Beckmann reactions were integrated with ethyl acetate according to the procedure described immediately below and in Table 12.

To a stirred mixture of 4-HAP (100.0 g), hydroxylamine sulfate (63.6 g), and water (191 mL) heated to 80° C. was added a solution of sodium hydroxide (30.5 g) in water (122 mL) over a period not longer than 30 seconds. The resulting stirred mixture was then refluxed under air at about 103° C. for 45–60 minutes before adding 223–318 g of ethyl acetate (either fresh or the distillate from a previous batch's azeotropic drying step). Reflux of ethyl acetate/water azeotrope cooled the stirred mixture to about 70° C. After having been stirred for about three minutes, the hot, solid-free mixture was allowed to separate into two liquid phases. The hot, solid-free aqueous phase was drained from the hot, solid-free ester phase, to which was added the ethyl acetate filtrate (123.0–284.0 g) from the previous batch's Beckmann reaction mixture. This ethyl acetate filtrate contained APAP, 4-HAP oxime, and 4-HAP as its most significant solutes.

The resulting 4-HAP oxime/ethyl acetate mixture was dried by azeotropic distillation as follows. The 4-HAP oxime/ethyl acetate mixture was stirred and refluxed under nitrogen at about 58°–64° C. and about 400 torr absolute pressure while 39.42–61.35 g of aqueous phase was removed from the reflux condensate with a Dean-Stark trap. After addition of KI (0.200 g) and fresh make-up ethyl acetate (45–225 g), azeotropic drying of the stirred 4-HAP oxime/ethyl acetate mixture was then continued by distillation through a 1" diameter, ten-tray Oldershaw column under nitrogen at about 400 torr absolute pressure with a 3:1 or a 1:1 reflux:take-off ratio. While 220–440 mL of ethyl acetate distillate was collected, the temperature of the undistilled residue rose from about 64° C. to about 75° C. The resulting undistilled residue was a substantially dry 4-HAP oxime/ethyl acetate mixture.

In Example 113, an aqueous slurry consisting of activated carbon (1.00 g), sodium dithionite (0.10 g), and water (2.2 mL) was added to the wet 4-HAP oxime/ethyl acetate mixture just before azeotropic drying with the Dean Stark trap was started. In Examples 114, 115, 117, and 118, activated carbon (1.0 g) was added to the 4-HAP oxime/ethyl acetate mixture after azeotropic drying with the Dean Stark trap had been completed and before azeotropic drying with the Oldershaw column was started.

A solid Vilsmeier reagent was prepared by stirring DMF (1.3–2.3 mL) and thionyl chloride (0.8–1.3 mL) in ethyl acetate (15–30 mL) at about 23° C. under nitrogen for about 20 minutes. The ethyl acetate suspension of the solid Vilsmeier reagent was then added as the Beckmann reaction catalyst in about 15 portions over about 30 minutes to the 4-HAP oxime/ethyl acetate mixture dried by azeotropic distillation. During the catalyst addition, the Beckmann reaction mixture was stirred under air-free conditions at a temperature of about 45°–51° C. maintained by ethyl acetate reflux at about 228 torr absolute pressure. After all catalyst had been added, the stirred Beckmann reaction mixture was allowed to cool to about 40° C. over about 15 minutes before being chilled to about 25° C.

In Examples 113–115, the acetaminophen product was neutralized after filtration. Nearly all of the residual ester left on the APAP filter cake was then removed by washing with the aqueous phase resulting from extraction of the oximation product with ester. The following procedure was used for Examples 113–115.

The Beckmann reaction mixture was filtered under air, and the ethyl acetate filtrate was transferred to a separatory funnel. The crude solid APAP filter cake, which still contained about 35 g of ethyl acetate that could not be removed by filtration, was slurried at about 25° C. with the aqueous phase from extraction of the oximation reaction mixture. The resulting aqueous APAP slurry was stirred at about 25° C. while being neutralized to about pH 6–6.5 by addition of 20 wt % aqueous sodium hydroxide (80–110 drops). The neutralized slurry was filtered to wash most of the ethyl acetate off the crude neutralized solid APAP with the aqueous phase. The aqueous wash liquor filtrate, which contained the ethyl acetate washed off the crude neutralized solid APAP, was added to the ethyl acetate filtrate in the separatory funnel. The contents of the separatory funnel were mixed well and then allowed to settle to extract the aqueous wash liquor filtrate with the ethyl acetate filtrate. Such extraction permits transfer of ethyl acetate and recyclable aromatics such as 4-HAP oxime from the aqueous wash liquor filtrate to the ethyl acetate filtrate phase.

The aqueous phase was drained from the ethyl acetate phase in the separatory funnel and was used to reslurry and wash the crude neutralized solid APAP. After filtration of the resulting slurry, the aqueous wash liquor filtrate was remixed with the ethyl acetate phase in the separatory funnel, and the resulting mixture was allowed to settle.

The procedure of the previous paragraph was repeated five more times. The resulting aqueous phase is considered to be a waste stream in Table 12. The resulting ethyl acetate filtrate phase was retained for recycle to the ethyl acetate phase from extraction of the next batch's aqueous oximation product. The neutralized and washed solid APAP was purified by known methods. Results are shown in Table 12.

In Examples 116–118, the acetaminophen product was at least partially neutralized before filtration. Nearly all of the residual ester left on the APAP filter cake was removed by washing with the aqueous phase resulting from extraction of the oximation product with ester. The following procedure was used for Examples 116–118.

Aqueous NaOH (20 wt %; 40–70 drops) was added to a 30 mL aliquot of the aqueous phase resulting from extraction of the crude oximation reaction mixture with ethyl acetate. This aliquot was then mixed with the crude Beckmann reaction mixture by stirring for about three minutes at about 25° C. The resulting mixture was filtered under air, and the wet ethyl acetate filtrate was transferred to a separatory funnel. The partially neutralized crude solid APAP filter cake, which still contained about 35 g of ethyl acetate that could not be removed by filtration, was slurried at about 25° C. with the remainder of the aqueous phase from extraction of the crude oximation reaction mixture. The resulting aqueous APAP slurry was filtered to wash most of the ethyl acetate off the solid APAP with the aqueous phase. The aqueous wash liquor filtrate, which contained the ethyl acetate washed off the solid APAP, was added to the wet ethyl acetate filtrate in the separatory funnel. Additional 20 wt % aqueous sodium hydroxide (20-30 drops) was also added to the separatory funnel. The contents of the separatory funnel were mixed well and then allowed to settle to extract the aqueous wash liquor filtrate with the ethyl acetate filtrate. Such extraction permits transfer of ethyl acetate and recyclable aromatics such as 4-HAP oxime from the aqueous wash liquor filtrate to the ethyl acetate filtrate phase.

The aqueous phase (pH of about 5.5-6.0) was drained from the ethyl acetate phase in the separatory funnel and was used to reslurry and wash the crude neutralized solid APAP. After filtration of the resulting slurry, the aqueous wash liquor filtrate was remixed with the ethyl acetate phase in the separatory funnel, and the resulting mixture was allowed to settle.

The procedure of the previous paragraph was repeated four more times. The resulting aqueous phase is considered to be a waste stream in Table 12. The resulting ethyl acetate filtrate phase was retained for recycle to the ethyl acetate phase from extraction of the next batch's aqueous oximation product. The neutralized and washed solid APAP was purified by known methods. Results are shown in Table 12.

EXAMPLES 119-121

In Examples 119-222, oximation and Beckmann reactions were integrated with n-butyl acetate. The crude solid APAP product was filtered, washed with n-butyl acetate, neutralized in water, and then freed from residual n-butyl acetate by water-assisted distillation. In the following procedure for Examples 119-121, figures in parenthetical triplets correspond to Example 119, Example 120, and Example 121, respectively.

To a stirred mixture of 4-HAP (1,360 g), hydroxylamine sulfate (865 g), and water (2,596 mL) heated to 80° C. was added a solution of sodium hydroxide (414.8 g) in water (1,659 mL) over about one minute. The resulting stirred mixture was then heated to about 100° C. for about 45 minutes before adding n-butyl acetate (4.0 L, 4.5 L, 4.0 L) consisting of the wash liquor (2.2 L, 2.0 L, 2.1 L) from the n-butyl acetate wash of the previous batch's crude solid APAP product, the second n-butyl acetate extract (1,603.6 g, 1,709 g, 1,729.5 g) of the aqueous phase from the previous batch's oximation reaction, and the n-butyl acetate phase (0 mL, 600 mL, 0 mL) of the azeotrope distilled off the hot aqueous solution of APAP product from the previous batch. After having been stirred for about five minutes, the hot, solid-free mixture of n-butyl acetate and aqueous oximation products was allowed to separate into two liquid phases over about three minutes. The hot, solid-free aqueous phase was drained from a hot, solid-free solution of 4-HAP oxime in n-butyl acetate. Fresh make-up n-butyl acetate (909 g, 0 g, 0 g) and the n-butyl acetate phase (590 mL, 0 mL, 0 mL) of the azeotrope distilled off the hot aqueous solution of APAP product from the previous batch were then added to the solution of 4-HAP oxime in n-butyl acetate.

The 4-HAP oxime/n-butyl acetate solution was dried by azeotropic distillation as follows. The 4-HAP oxime/n-butyl acetate solution was stirred and refluxed under nitrogen at about 62°-74° C. and about 71-112 mm HgA pressure while about 425-433 g of aqueous phase was removed from the reflux condensate with a Dean-Stark trap. After addition of activated carbon (13.6 g, 27.2 g, 27.2 g), the n-butyl acetate filtrate (2,240 g, 3,000 g, 3,360 g) from the previous batch's Beckmann reaction mixture, and fresh make-up n-butyl acetate (0 g, 612 g, 0 g), azeotropic drying of the stirred 4-HAP oxime/n-butyl acetate solution was continued by refluxing the solution at about 70°-74° C. and about 73-97 mm HgA pressure for about half an hour while additional aqueous phase was removed from the reflux condensate with the Dean-Stark trap. The 4-HAP oxime/n-butyl acetate solution was then recirculated through a filter at about 65°-72° C. to remove activated carbon. After addition of KI (2.72 g), azeotropic drying of the stirred 4-HAP oxime/n-butyl acetate solution was continued with the Dean-Stark trap at about 70°-74° C. and about 73-97 mm HgA pressure until the reflux condensate was substantially free of a separate aqueous phase. The total amount of aqueous phase removed by the Dean-Stark trap was 450-463 g. Azeotropic drying of the stirred 4-HAP oxime/n-butyl acetate solution was then completed by simple distillation at 72°-73° C. While about 4 L of n-butyl acetate distillate was collected, the distillation pressure was reduced from about 92 mm HgA to about 72 mm HgA. The resulting undistilled residue was a substantially dry 4-HAP oxime/n-butyl acetate mixture.

The aqueous phase from extraction of the aqueous oximation products with n-butyl acetate was extracted again, this time at about 25° C. with about 2 L of the n-butyl acetate distillate from the azeotropic drying step. The resulting n-butyl acetate extract (1,709 g, 1,729.5 g, 1,710.7 g) was saved for recycle to the 4-HAP oxime extraction step of the next batch. The resulting aqueous phase is considered to be a waste stream in Table 13.

A solid Vilsmeier reagent was prepared by stirring DMF (32 mL) and thionyl chloride (16 mL) in n-butyl acetate (250 mL) at about 23° C. under nitrogen for about 20 minutes. The n-butyl acetate suspension of the solid Vilsmeier reagent was then added as the Beckmann reaction catalyst in about 13-16 portions over about 64-69 minutes to the 4-HAP oxime/n-butyl acetate mixture dried by azeotropic distillation. During the catalyst addition, the Beckmann reaction mixture was stirred under air-free conditions at a temperature of about 42°-52° C. maintained by n-butyl acetate reflux at about 18 torr absolute pressure. After all catalyst had been added, the stirred Beckmann reaction mixture was allowed to cool to 31°-33° C. over 16-23 minutes before being chilled to 10° C.

The Beckmann reaction mixture was then filtered, and the resulting n-butyl acetate filtrate (3,000 g, 3,371 g, 3,058 g) was saved for recycle to the azeotropic drying step of the next batch. The crude solid APAP product filtered off the Beckmann reaction mixture was washed at about 25° C. with about 2 L of the n-butyl acetate distillate from the azeotropic drying step. The n-butyl acetate wash liquor, which contained dissolved recyclable aromatics including unreacted 4-HAP oxime, was filtered off the crude solid APAP product and saved for recycle to the 4-HAP oxime extraction step of the next batch.

The crude solid APAP filter cake, which still contained about 400 mL of n-butyl acetate that could not be removed by filtration, was slurried in about 6 L of water. The resulting aqueous APAP slurry was stirred at about 25° C. while being neutralized to about pH 6–6.5 by addition of 5 wt % aqueous sodium hydroxide (100 g, 100 g, 160 g). The neutralized aqueous APAP slurry was stirred and heated to about 100° C. under nitrogen to dissolve the solid APAP. The resulting solution was then distilled with stirring at about 97°–104° C. and about 0–3 psig pressure to remove an azeotrope distillate consisting of an upper n-butyl acetate phase (600 mL, 348 mL, 315 mL) and a lower aqueous phase (250 mL, 222 mL, 265 mL). The n-butyl acetate phase was separated from the aqueous phase and was recycled to the 4-HAP oxime extraction step of a subsequent batch. The resulting undistilled residue was then chilled to about 10° C. to recrystallize the dissolved APAP. The recrystallized APAP was filtered and further purified by known methods. Results are shown in Table 13.

EXAMPLE 122

In this example, 4-HAP oxime was converted to recrystallized APAP in a single vessel without filtration of the ester Beckmann reaction mixture. After addition of water, the last portion of ester solvent was removed by water-assisted distillation.

The catalyst mixture for the Beckmann rearrangement was prepared as follows. Acetonitrile (5 mL) was added to solid trimethyloxonium tetrafluoroborate (5.14 g), and the resulting mixture was stirred at about 25° C. under nitrogen for 30 minutes before more acetonitrile (4 mL) was added. All solids dissolved while the resulting mixture was stirred at about 25° C. under nitrogen for an additional 30 minutes. Stirring was then discontinued, and colorless crystals precipitated while the mixture stood under nitrogen at about 25° C. for about 24 hours. All excess acetonitrile was then evaporated from the mixture under vacuum at 0°–25° C. The resulting colorless crystalline residue, which is known to be about 4.96 g of N-methylacetonitrilium tetrafluoroborate from S. C. Eyley, R. G. Giles, and H. Heaney, Tetrahedron Letters, Vol. 26. No. 38, p. 4,649, 1985, was resuspended in n-butyl acetate (30 mL) under nitrogen to provide the catalyst mixture for the Beckmann rearrangement.

The n-butyl acetate suspension of N-methylacetonitrilium tetrafluoroborate was then added as the Beckmann reaction catalyst in about 15 portions over about 80 minutes to a stirred suspension of 4-HAP oxime (200.0 g) in n-butyl acetate (about 430 mL). During the catalyst addition, the Beckmann reaction mixture was stirred under air-free conditions at a temperature of about 48° C. maintained by n-butyl acetate reflux at about 30 mm HgA pressure. An additional 30 mL of n-butyl acetate was added to the last portions of solid catalyst to assist suspension and addition to the Beckmann reaction mixture. The stirred reaction mixture was allowed to cool to 30° C., and about 275 mL of the n-butyl acetate solvent was distilled off the stirred Beckmann reaction mixture at about 30° C. and 3 mm HgA pressure.

Water (1.0 L) was added to the remaining n-butyl acetate slurry of Beckmann reaction products, and the resulting mixture was stirred at about 25° C. while being neutralized to about pH 6 by addition of 25 wt % aqueous sodium hydroxide (10 g) followed by concentrated aqueous HCl (70 drops). Substantially all n-butyl acetate was then removed from the stirred neutralized Beckmann reaction products by distillation as a water azeotrope at about 24° C. and about 10–20 mm HgA pressure. The resulting distillation residue was then stirred and heated to about 83° C. under 1 atm of nitrogen to completely dissolve the solid Beckmann reaction products. The resulting stirred aqueous solution precipitated recrystallized APAP on chilling to 5° C. The recrystallized APAP was filtered from the aqueous mother liquor, washed with water (5° C., 200 mL), and then dried at about 0.05 mm HgA pressure to provide the purified APAP. Results are shown in Table 13.

EXAMPLE 123

The APAP synthesis of Example 122 was repeated with N-isopropylacetonitrilium tetrachloroferrate as the Beckmann rearrangement catalyst instead of N-methylacetonitrilium tetrafluoroborate.

The catalyst mixture for the Beckmann rearrangement was prepared under nitrogen with magnetic stirring and ice bath cooling as follows. A mixture of anhydrous ferric chloride (8.10 g) and isopropyl chloride (35 mL) was stirred under nitrogen for 30 minutes while being chilled in an ice bath. While continuing ice bath cooling and stirring under nitrogen, acetonitrile (2.65 mL) was then added dropwise over ten minutes. The resulting red-orange suspension was then stirred under nitrogen with ice bath cooling for 16 hours before the excess isopropyl chloride was evaporated under vacuum at 0°–25°· C. The resulting brownish-yellow solid residue, which is known to be about 14.07 g of N-isopropylacetonitrilium tetrachloroferrate from R. Fuks, Tetrahedron, Vol. 29 (1973), p. 2,150, was resuspended in n-butyl acetate (30 mL) under nitrogen and used promptly as the catalyst mixture for the Beckmann rearrangement.

The n-butyl acetate suspension of N-isopropylacetonitrilium tetrachloroferrate was then added as the Beckmann reaction catalyst in about 15 portions over about 57 minutes to a stirred suspension of 4-HAP oxime (200.0 g) in n-butyl acetate (about 450 mL). During the catalyst addition, the Beckmann reaction mixture was stirred under air-free conditions at a temperature of about 43°–50° C. maintained by n-butyl acetate reflux at about 25 mm HgA pressure. About 275 mL of the n-butyl acetate solvent was then distilled off the stirred Beckmann reaction mixture at about 30° C. and 10 mm HgA pressure.

Water (0.1 L) was added to the remaining n-butyl acetate slurry of Beckmann reaction products, and the resulting mixture was stirred at about 25° C. while being neutralized to about pH 6.5 by addition of 25 wt % aqueous sodium hydroxide (23.1 g). Substantially all n-butyl acetate was then removed from the stirred neutralized Beckmann reaction products by distillation as a water azeotrope at about 29° C., 54 mm HgA pressure to 36° C., 36 mm Hg pressure. The resulting distillation residue was then stirred and heated to about 90° C. under 1 atm of nitrogen to completely dissolve the solid Beckmann reaction products. The resulting stirred aqueous solution precipitated recrystallized APAP on chilling to 3° C. The recrystallized APAP was filtered from the aqueous mother liquor, washed with water (200 mL), and then dried at about 0.05 mm HgA pressure to provide the purified APAP. Results are shown in Table 13.

EXAMPLE 124

In this example, 4-HAP is converted to recrystallized APAP in a single vessel without filtration of the ester Beckmann reaction mixture. After addition of water, the last portion of ester solvent is removed by steam-assisted distillation.

To a stirred mixture of 4-HAP (200 g), hydroxylamine sulfate (127.2 g), and water (382 mL) heated to 80° C. is added a solution of sodium hydroxide (61 g) in water (244 mL) over about one minute. The resulting stirred mixture is then heated to about 100° C. for about 45 minutes before adding n-butyl acetate (about 720 mL). After being stirring for about five minutes, the hot, solid-free mixture of n-butyl acetate and aqueous oximation products is allowed to separate into two liquid phases over about three minutes. The hot, solid-free aqueous phase is drained from a hot, solid-free solution of 4-HAP oxime in n-butyl acetate.

More n-butyl acetate (480 mL) is added to the 4-HAP oxime/n-butyl acetate solution, and the resulting mixture is dried by azeotropic distillation as follows. The 4-HAP oxime/n-butyl acetate mixture is stirred and refluxed under nitrogen at about 55°-65° C. and about 80 mm HgA pressure while about 50 g of aqueous phase is removed from the reflux condensate with a Dean-Stark trap and until the reflux condensate is substantially free of a separate aqueous phase. Azeotropic drying of the stirred 4-HAP oxime/n-butyl acetate mixture is then completed by simple distillation at about 80 mm HgA pressure. While about 720 mL of n-butyl acetate distillate is collected, the temperature of the undistilled residue rises from about 65° C. to about 75° C. Potassium iodide (about 0.4 g) is then added to the resulting undistilled residue, which is a substantially dry mixture of 4-HAP oxime in n-butyl acetate.

A suspension of N-methylacetonitrilium tetrafluoroborate (5.5 g) in n-butyl acetate (about 50 mL) is then added as the Beckmann reaction catalyst in about 15 portions over about 80 minutes to the dry mixture of 4-HAP oxime in n-butyl acetate. During the catalyst addition, the Beckmann reaction mixture is stirred under air-free conditions at a temperature of about 48° C. maintained by n-butyl acetate reflux at about 30 mm HgA pressure. The stirred Beckmann reaction mixture is then cooled to about 25° C. before addition of water (about 500 mL). The resulting mixture is stirred at about 25° C. while being neutralized to about pH 6 by addition of 25 wt % aqueous sodium hydroxide. Water vapor (i.e., steam) is then passed into the stirred slurry of neutralized Beckmann reaction products to remove substantially all n-butyl acetate by distillation as a water azeotrope at about 24° C. and about 10-20 mm HgA pressure. Water is added to the resulting aqueous slurry of neutralized Beckmann reaction products as necessary to increase the slurry's water content to about 1.0 L. The APAP product is then recrystallized and recovered as described in Example 122. All n-butyl acetate distillates are recycled to the next batch.

EXAMPLE 125

The APAP synthesis of Example 124 is repeated with the following modifications. Activated carbon (2.00 g) is added to the mixture of 4-HAP oxime and n-butyl acetate after azeotropic distillation with the Dean-Stark trap and before distillative removal of the 720 mL of n-butyl acetate distillate. Prior to recrystallization of the APAP product, the hot aqueous solution of Beckmann reaction products is recirculated through a filter to remove the activated carbon.

The following Tables 1-13 use the following abbreviations:

Ac: the acetyl radical $CH_3C=O$
acct: accountability
APAP: N-acetyl-p-aminophenol (acetaminophen)
$ArSO_3Na$: sodium 4-hydroxybenzenesulfonate
conv: conversion
CTMAB: cetyltrimethyl ammonium bromide
DMA: N,N-dimethylacetamide
DMF: N,N-dimethylformamide
Et: the ethyl radical $CH_3CH_2$
4-HAP: 4-hydroxyacetophenone
HPLC: high pressure (performance) liquid chromatography
limit of color: the 420 nm absorbance of the supernate obtained from centrifugation of a slurry of 10 g of solid sample in 10 mL of methanol
MHBA: N-methyl-p-hydroxybenzamide
MSA: methanesulfonic acid
NMP: N-methylpyrrolidinone
others: all HPLC-detectable aromatics not specifically listed
oxime: 4-hydroxyacetophenone oxime
Oxime-O-$SO_3K$: potassium 4-hydroxyacetophenone oxime-O-sulfonate
Ph: the phenyl radical $C_6H_5$
PPA: polyphosphoric acid
ppm: parts per million by weight
SDS: sodium dodecyl sulfate
$SO_3.Pyr$: sulfur trioxide-pyridine complex
temp: temperature
p-TSA: p-toluenesulfonic acid
wt: weight Names of some reagents shown in Tables 1-13 are indicated below:

$SOCl_2$: thionyl chloride
$CH_3SO_2Cl$: methanesulfonyl chloride
$CF_3SO_2Cl$: trifluoromethanesulfonyl chloride
$CF_3SO_3H$: trifluoromethanesulfonic acid
MSA Anhydride: methanesulfonic anhydride
p-TSA Anhydride: p-toluenesulfonic anhydride
$ClSO_3H$: chlorosulfonic acid
$P_2O_5$: phosphorus pentoxide
$(CH_3O)_2SO$: dimethyl sulfite
$POCl_3$: phosphorus oxytrichloride
$PhPOCl_2$: phenylphosphonic dichloride
$Ph_2POCl$: diphenylphosphinic chloride
$Et_2O.BF_3$: boron trifluoride etherate
$((AcO)_2B)_2O$: tetraacetyl diborate
$CH_2CN^+CH_3BF_4^-$: N-methylacetonitrilium tetrafluoroborate
$CCl_3CO_2H$: trichloroacetic acid
$CCl_3COCl$: trichloroacetyl chloride
$(CCl_3CO)_2O$: trichloroacetic anhydride
$CF_3CO_2H$: trifluoroacetic acid
$(CF_3CO)_2O$: trifluoroacetic anhydride
$NEt_3$: triethylamine
$CCl_3CO_2SO_2CH_3$: Mixed anhydride of trichloroacetic and methanesulfonic acids
$ClCO_2CH_3$: methyl chloroformate
$ClCON(CH_3)_2$: N,N-dimethylcarbamyl chloride
$CH_3NCO$: methyl isocyanate
$ClCO_2CCl_3$: trichloromethyl chloroformate (diphosgene)
$ClCOCO_2Et$: ethyl oxalyl chloride ClCOCOCl: oxalyl chloride
CF₃CO₂Na: sodium trifluoroacetate
CH₃CO₂Na: sodium acetate
$(NH_4)^+(H_2PO_4)^-$: ammonium dihydrogen phosphate
$Na_2S_2O_5$: sodium metabisulfite
$B(OCH_3)_3$: trimethyl borate In the following Tables 1–13, "accountability" is 100% times the sum total moles of all HPLC-detectable aromatics in all recovered outputs divided by the sum total moles of all aromatics in all feeds. If an aromatic's "net make" is the total moles of that aromatic in all recovered outputs minus the total moles of that aromatic in all feeds, then that aromatic's "efficiency" is 100% times that aromatic's net make divided by the sum total net makes of all HPLC-detectable aromatics with a positive net make. The unconverted fraction of oxime is the total moles of all oxime in all recovered outputs divided by the total moles of all oxime in all feeds. The normalized unconverted fraction of oxime is 100 times the unconverted fraction of oxime divided by the accountability defined above. "Conversion" is 100% times the difference of 1.0 and the normalized unconverted fraction of oxime. In all of these calculations, all 4-HAP fed to an oximation reaction is considered to be oxime feed and not 4-HAP feed.

In Tables 12 and 13, "unrecycled output" consists of the purified APAP and the "waste streams." For Examples 122 and 123 in Table 13, the "waste streams" consist of the aqueous mother and wash liquors from the APAP recrystallization. For Examples 119–121 in Table 13, the "waste streams" consist of the aqueous mother and was liquors from the APAP recrystallization and the aqueous phase resulting from the second extraction of the oximation reaction mixture with butyl acetate. For Examples 113–118 in Table 12, the "waste streams" consist of the aqueous mother and wash liquors from an APAP recrystallization and the aqueous phase resulting from extraction of the oximation reaction mixture and subsequent neutralization and washing of the crude solid APAP product. All other aromatic-containing output from Examples 113–121 was recycled to the next batch. All aromatic-containing output from Examples 122 and 123 was the above-described unrecycled output.

None of the figures in Tables 1–13 include mechanical losses or losses to activated carbon/Celite filter cakes. It is believed that such losses account for substantially all aromatic products not represented in Tables 1, 12, and 13. It is therefore further believed that with minimization of such losses in commercial scale production, actual APAP yields would closely approach the figures shown in Tables 12–13 for "Purified APAP" " As a Molar Percentage of all Unrecycled Output."

In the following claims, "filtering" and "filtration" are to be interpreted as generic terms fully embracing the actions and concepts of centrifuging and centrifugation.

TABLE 1

| Example No. | 1 | 2 | 3 | 4 | 5 | 6 | 7 | 8 | 9 | 10 | 11 | 12 |
|---|---|---|---|---|---|---|---|---|---|---|---|---|
| 4-HAP Oxime Conversion (%) | 99.44 | 98.94 | 99.51 | 97.56 | 97.22 | 98.94 | 99.64 | 99.24 | 97.18 | 99.49 | 98.94 | 92.48 |
| Product Efficiencies (%) | | | | | | | | | | | | |
| APAP | 98.52 | 98.98 | 99.01 | 98.78 | 98.97 | 97.95 | 97.52 | 97.21 | 83.75 | 98.01 | 96.81 | 96.09 |
| 4-HAP | 1.12 | 0.61 | 0.54 | 0.66 | 0.22 | 1.85 | 2.03 | 2.09 | 3.19 | 1.71 | 2.35 | 3.21 |
| Other By-Products | 0.36 | 0.41 | 0.46 | 0.56 | 0.81 | 0.19 | 0.45 | 0.70 | 13.06[1] | 0.29 | 0.84 | 0.69 |
| Yield of Purified APAP (%) | 75.75 | | | 75.91 | | 79.94 | 73.66 | | | 75.10 | 56.03 | 54.00 |
| Analysis of Purified APAP | | | | | | | | | | | | |
| 4-HAP (wt %) | 0.009 | | | 0.015 | | 0.020 | 0.017 | | | 0.000 | 0.002 | 0.000 |
| 4-HAP Oxime (wt %) | 0.001 | | | 0.000 | | 0.000 | 0.000 | | | 0.000 | 0.000 | 0.000 |
| Other Impurities (wt %) | 0.015 | | | 0.060 | | 0.020 | 0.147 | | | 0.015 | 0.042 | 0.013 |
| Limit of Color | 0.011 | | | 0.038 | | 0.008 | 0.030 | | | 0.025 | 0.048 | 0.053 |

[1] Most of this figure (12.47%) is due to p-aminophenol.

sist of the aqueous mother and wash liquors from the

TABLE 2

| Example No. | 13 | 14 | 15 | 16 | 17 | 18 | 19 | 20 | 21 | 22 | 23 |
|---|---|---|---|---|---|---|---|---|---|---|---|
| Catalyst Components | $SOCl_2$ 1.3 mL | $SOCl_2$ 0.11 mL | $SOCl_2$ 0.9 mL | $SOCl_2$ 0.7 mL | p-TSA Anhydride 4.9 g | MSA Anhydride 3.0 g | $CH_3SO_2Cl$ 1.89 mL | $CH_3SO_2Cl$ 1.4 mL | $CH_3SO_2Cl$ 0.9 mL | $CF_3SO_2Cl$ 1.8 mL | $CF_3SO_3H$ 3.0 g $ClSO_3H$ 1.2 g |
| Temp (°C.) | 53 | 50 | 51 | 51 | 50 | 50 | 51 | 48 | 51 | 67 | 70 |
| Time (min) | 25 | 37 | 35 | 35 | 60 | 60 | 130 | 40 | 78 | 134 | 90 |
| Oxime Conv (%) | 99.2 | 98.2 | 89.0 | 59.3 | 93.5 | 95.9 | 96.3 | 94.7 | 82.2 | 94.2 | 12.8 |
| Oxime Acct (%) | 95.4 | 95.9 | 90.9 | 85.6 | | | 95.9 | 77.2 | 84.3 | 86.4 | |
| Efficiencies (%) to: | | | | | | | | | | | |
| APAP | 98.9 | 98.9 | 98.8 | 96.8 | | | 98.0 | 98.8 | 97.9 | 98.7 | |
| MHBA | 0.077 | 0.049 | 0.050 | 0.075 | | | 0.120 | 0.025 | 0.040 | 0.131 | |
| Yields (%): | | | | | | | | | | | |
| APAP | 93.7 | 93.2 | 80.0 | 49.1 | 88.1 | 93.1 | 90.6 | 72.2 | 67.9 | 80.4 | 9.7 |
| MHBA | 0.073 | 0.046 | 0.040 | 0.038 | 0.052 | 0.061 | 0.111 | 0.018 | 0.028 | 0.107 | 0.005 |
| Precipitated Solids: | | | | | | | | | | | |
| Yield (%) | 87.6 | 87.6 | 73.2 | 39.6 | 79.9 | 85.6 | | | | 74.0 | 2.1 |
| MHBA (ppm) | 296 | 186 | 39 | 0 | 67 | 107 | 151 | 50 | 26 | 897 | 22 |

TABLE 3

| Example No. | 24 | 25 | 26 | 27 | 28 | 29 | 30 |
|---|---|---|---|---|---|---|---|
| Catalyst Components | MSA:P$_2$O$_5$ 10:1 w/w (2 mL Total) | SO$_3$ 0.62 mL CH$_3$SO$_3$H 1.3 mL | SO$_3$ (65% Oleum) 1.2 mL | SO$_3$ 1.0 mL | SO$_3$.Pyr 2.03 g | Oxime-O—SO$_3$K 4.6 g | (CH$_3$O)$_2$SO 1.7 mL |
| Additives Charged with Oxime | | | | | | H$_2$SO$_4$ 3.00 g | |
| Temp (°C.) | 50 | 70 | 70 | 53 | 68 | 70 | 70 |
| Time (min) | 60 | 91 | 120 | 72 | 183 | 102 | 120 |
| Oxime Conv (%) | 45.2 | 19.6 | 6.7 | 5.6 | 2.0 | 67.2 | 25.3 |
| Oxime Acct (%) | | | | | 63.5 | | |
| Efficiencies (%) to: | | | | | | | |
| APAP | | | | | | 0.0 | |
| MHBA | | | | | | 0.000 | |
| Yields (%): | | | | | | | |
| APAP | 22.8 | 18.6 | 6.0 | 3.2 | 0.0 | 5.2 | 0.3 |
| MHBA | 0.001 | 0.009 | 0.060 | 0.007 | 0.000 | 0.002 | 0 |
| Precipitated Solids: | | | | | | | |
| Yield (%) | 10.1 | 19.4 | 30.5 | 40.0 | 39.8 | 14.0 | 58.5 |
| MHBA (ppm) | 78 | 33 | 608 | 64 | 0 | 45 | 0 |

TABLE 4

| Example No. | 31 | 32 | 33 | 34 | 35 | 36 | 37 | 38 | 39 |
|---|---|---|---|---|---|---|---|---|---|
| Catalyst Components | POCl$_3$ 1.6 mL | PhPOCl$_2$ 2.24 mL | Ph$_2$POCl 2.6 mL | P$_2$O$_5$ 3.6 g | PPA 2.01 g | H$_3$PO$_4$ 1.4 g CCl$_3$CO$_2$H 3.3 g | Et$_2$O.BF$_3$ 4.8 mL | B(OEt)$_3$ 2.3 mL | ((AcO)$_2$B)$_2$O 2.0 g |
| Temp (°C.) | 50 | 50 | 61→83 | 70 | 71 | 70 | 80 | 90 | 70 |
| Time (min) | 20 | 25 | 105 | 120 | 73 | 120 | 330 | 120 | 120 |
| Oxime Conv (%) | 99.4 | 99.3 | 80.7 | 60.2 | 2.9 | 1.8 | 65.9 | 1.3 | 0.9 |
| Oxime Acct (%) | 97.6 | 96.8 | 93.4 | | 73.2 | | 96.6 | 93.3 | |
| Efficiencies (%) to: | | | | | | | | | |
| APAP | 97.5 | 98.8 | 96.6 | | 57.7 | | 91.4 | 2.2 | |
| MHBA | 0.080 | 0.086 | 0.036 | | 0.591 | | 0.033 | 0.000 | |
| Yields (%): | | | | | | | | | |
| APAP | 94.5 | 95.0 | 72.8 | 35.0 | 1.2 | 0.4 | 58.2 | 0.0 | 0.0 |
| MHBA | 0.078 | 0.083 | 0.027 | 0.049 | 0.012 | 0 | 0.021 | 0.000 | 0 |
| Precipitated Solids: | | | | | | | | | |
| Yield (%) | 88.6 | 88.7 | 60.7 | 50.0 | 53.0 | 60.7 | 71.3 | 54.8 | 44.5 |
| MHBA (ppm) | 682 | 381 | 147 | 370 | 15 | 0 | 85 | 0 | 0 |

TABLE 5

| Example No. | 40 | 41 | 42 | 43 | 44 | 45 |
|---|---|---|---|---|---|---|
| Catalyst Components | CH$_3$CN$^+$CH$_3$ BF$_4^-$ (2.48 g, 17.37 mmol) | (CCl$_3$CO)$_2$O 5.0 mL | (CF$_3$CO)$_2$O 5.0 mL | (CF$_3$CO)$_2$O 3.0 g HCl sparged separately | CCl$_3$COCl 2.5 mL | CCl$_3$COCl 2.8 mL Oxime 4.0 g NEt$_3$ 3.5 mL |
| Additives Charged with Oxime | | | | | | CF$_3$CO$_2$H 3.9 mL |
| Temp (°C.) | 48 | 65–71 | 68–73 | 70 | 65–70 | 70 |
| Time (min) | 80 | 139 | 133 | 120 | 57 | 15 |
| Oxime Conv (%) | 98.2 | 96.9 | 99.5 | 92.9 | 97.7 | 92.3 |
| Oxime Acct (%) | 97.2 | 91.6 | 96.7 | | 93.3 | |
| Efficiencies (%) to: | | | | | | |
| APAP | 98.8 | 97.9 | 97.9 | | 98.6 | |
| MHBA | 0.000 | 0.000 | 0.000 | | 0.025 | |
| Yields (%): | | | | | | |
| APAP | 94.3 | 87.0 | 94.2 | 101.3 | 89.9 | 87.8 |
| MHBA | 0.000 | 0.000 | 0.000 | 0.162 | 0.023 | 0.003 |
| Precipitated Solids: | | | | | | |
| Yield (%) | 87.7 | 79.4 | 85.8 | 99.8 | 83.9 | 80.4 |
| MHBA (ppm) | 0 | 0 | 0 | 687 | 132 | 10 |

| Example No. | 46 | 47 | 48 | 49 | 50 |
|---|---|---|---|---|---|
| Catalyst Components | CCl$_3$COCl 3.5 mL Oxime 5.3 g NEt$_3$ 4.3 mL | CCl$_3$CO$_2$H 9.8 g SOCl$_2$ 1.83 mL | SOCl$_2$ 1.0 mL | CCl$_3$CO$_2$SO$_2$CH$_3$ 2.5 g | CF$_3$CO$_2$H 3.0 mL |
| Additives | | | CF$_3$CO$_2$H | | |

TABLE 5-continued

|  |  |  | Charged with Oxime |  |  | 4.0 g NEt₃ 3.5 g |  |  |
|---|---|---|---|---|---|---|---|---|
|  |  |  | Temp (°C.) | 70 | 70 | 50 | 70 | 53 |
|  |  |  | Time (min) | 25 | 33 | 15 | 120 | 140 |
|  |  |  | Oxime Conv (%) | 85.8 | 99.4 | 72.9 | 80.0 | 2.1 |
|  |  |  | Oxime Acct (%) |  |  |  |  | 79.3 |
|  |  |  | Efficiencies (%) to: |  |  |  |  |  |
|  |  |  | APAP |  |  |  |  | 27.6 |
|  |  |  | MHBA |  |  |  |  | 0.000 |
|  |  |  | Yields (%): |  |  |  |  |  |
|  |  |  | APAP | 72.6 | 97.4 | 59.3 | 42.8 | 0.5 |
|  |  |  | MHBA | 0.002 | 0.071 | 0.001 | 0.012 | 0.000 |
|  |  |  | Precipitated Solids: |  |  |  |  |  |
|  |  |  | Yield (%) | 53.4 | 92.5 | 48.4 | 37.7 | 54.3 |
|  |  |  | MHBA (ppm) | 0 | 237 | 0 | 49 | 0 |

TABLE 6

| Example No. | 51 | 52 | 53 | 54 | 55 | 56 |
|---|---|---|---|---|---|---|
| Catalyst Components | CH₃COCl 1.0 mL | Ac₂O 1.3 mL H₂SO₄ 0.75 mL | 3-Nitro- Phthalic Anhydride 3.9 g | ClCO₂CH₃ 2.0 mL | ClCO₂CH₃ 2.0 mL | ClCON(CH₃)₂ 2.0 mL |
| Temp (°C.) | 88 | 71 | 70 | 70 | 70 | 70 |
| Time (min) | 65 | 133 | 90 | 128 | 128 | 131 |
| Oxime Conv (%) | 8.2 | 15.3 | 2.1 | 62.4 | 52.2 | 59.3 |
| Oxime Acct (%) | 60.3 | 59.7 |  | 72.9 | 48.5 | 69.2 |
| Efficiencies (%) to: |  |  |  |  |  |  |
| APAP | 58.4 | 74.7 |  | 83.1 | 85.1 | 93.3 |
| MHBA | 0.009 | 0.008 |  | 0.182 | 0.001 | 0.004 |
| Yields (%): |  |  |  |  |  |  |
| APAP | 2.9 | 6.8 | 0.1 | 37.8 | 21.5 | 38.3 |
| MHBA | 0.000 | 0.001 | 0 | 0.083 | 0.000 | 0.002 |
| Precipitated Solids: |  |  |  |  |  |  |
| Yield (%) | 7.8 | 23.7 | 53.7 | Above Results Before Precipitation | 15.3 | 30.6 |
| MHBA (ppm) | 58 | 29 | 0 |  | 17 | 56 |

| Example No. | 57 | 58 | 59 | 60 |
|---|---|---|---|---|
| Catalyst Components | CH₃NCO 2.0 mL | ClCO₂CCl₃ 1.0 mL | ClCOCO₂Et 1.5 mL | ClCOCOCl 2.0 mL |
| Temp (°C.) | 70 | 50 | 70–73 | 66–72 |
| Time (min) | 128 | 60 | 126 | 60 |
| Oxime Conv (%) | 16.2 | 99.2 | 74.9 | 95.8 |
| Oxime Acct (%) | 62.0 |  | 81.0 | 110.1 |
| Efficiencies (%) to: |  |  |  |  |
| APAP | 0.8 |  | 97.2 | 98.5 |
| MHBA | 0.000 |  | 0.003 | 0.116 |
| Yields (%): |  |  |  |  |
| APAP | 0.1 | 91.8 | 59.0 | 103.9 |
| MHBA | 0.000 | 0.190 | 0.002 | 0.122 |
| Precipitated Solids: |  |  |  |  |
| Yield (%) | 32.8 | 82.8 | 51.6 | 82.0 |
| MHBA (ppm) | 0 | 588 | 32 | 544 |

TABLE 7

| Example No. | 61 | 62 | 63 | 64 | 65 | 66 | 67 | 68 | 69 |
|---|---|---|---|---|---|---|---|---|---|
| Catalyst Components | DMF 4.0 mL SOCl₂ 2.0 mL | DMF 1.36 mL SOCl₂ 1.3 mL | DMF 1.4 mL SOCl₂ 1.3 mL | DMF 2.0 mL SOCl₂ 1.3 mL | DMF 2.0 mL SOCl₂ 1.3 mL | DMF 1.2 mL SOCl₂ 0.9 mL | DMF 1.07 mL SOCl₂ 0.7 mL | SOCl₂ 0.7 mL | SOCl₂ 1.1 mL |
| Additives Charged with Oxime |  |  |  |  |  |  |  | DMF 1.07 mL | DMF 6.0 mL |
| Temp (°C.) | 48–82 | 51–70 | 47–52 | 48–51 | 48–52 | 51 | 52 | 49–52 | 49–52 |
| Time (min) | 22 | 33 | 20 | 30 | 33 | 53 | 35 | 21 | 20 |
| Oxime Conv (%) | 99.2 | 99.2 | 97.1 | 91.0 | 89.2 | 87.3 | 75.4 | 84.0 | 96.0 |
| Oxime Acct (%) | 95.6 | 98.3 | 98.7 | 99.3 | 98.2 | 95.4 | 87.5 | 89.2 | 99.5 |
| Efficiencies (%) to: |  |  |  |  |  |  |  |  |  |
| APAP | 98.6 | 98.8 | 97.6 | 98.6 | 98.7 | 98.7 | 98.1 | 98.5 | 98.8 |
| MHBA | 0.036 | 0.059 | 0.027 | 0.006 | 0.009 | 0.000 | 0.000 | 0.003 | 0.015 |
| Yields (%): |  |  |  |  |  |  |  |  |  |
| APAP | 93.5 | 96.4 | 93.5 | 89.1 | 86.5 | 82.2 | 64.7 | 73.7 | 94.4 |
| MHBA | 0.034 | 0.058 | 0.026 | 0.005 | 0.008 | 0.000 | 0.000 | 0.002 | 0.014 |

TABLE 7-continued

| Example No. | 61 | 62 | 63 | 64 | 65 | 66 | 67 | 68 | 69 |
|---|---|---|---|---|---|---|---|---|---|
| Precipitated Solids: | | | | | | | | | |
| Yield (%) | 85.8 | 88.2 | 88.0 | 81.0 | 77.3 | 72.2 | 55.1 | 65.8 | 85.5 |
| MHBA (ppm) | 189 | 360 | 226 | 25 | 43 | 0 | 0 | 22 | 105 |

TABLE 8

| Example No. | 70 | 71 | 72 | 73 | 74 | 75 | 76 | 77 |
|---|---|---|---|---|---|---|---|---|
| Catalyst Components | DMF 3.0 mL POCl$_3$ 1.0 mL | DMF 3.0 mL POCl$_3$ 1.0 mL | DMF 3.0 mL POCl$_3$ 1.0 mL | DMF 3.6 mL POCl$_3$ 1.2 mL | DMF 3.6 mL POCl$_3$ 1.2 mL | DMF 3.6 mL POCl$_3$ 1.2 mL | DMF 3.0 mL POCl$_3$ 1.0 mL | DMF 3.0 mL POCl$_3$ 1.0 mL |
| Additives Charged with Oxime | | | | | | | | CF$_3$CO$_2$Na 5.4 g |
| Temp (°C.) | 25 | 25 | 35 | 25 | 25 | 25 | 50 | 50 |
| Time (min) | 90 | 60 | 24 | 60 | 54 | 60 | 60 | 60 |
| Oxime Conv (%) | 95.2 | 98.6 | 98.8 | 99.1 | 99.3 | 99.6 | 99.1 | 79.2 |
| Yields (%): | | | | | | | | |
| APAP | 90.7 | 91.2 | 115.8 | 96.9 | 97.2 | 91.4 | 102.6 | 49.7 |
| MHBA | 0.002 | 0.007 | 0.069 | 0.020 | 0.029 | 0.019 | 0.112 | 0.002 |
| Precipitated Solids: | | | | | | | | |
| Yield (%) | 86.3 | 83.8 | 96.4 | 89.2 | 89.6 | 85.5 | 84.1 | 42.4 |
| MHBA (ppm) | 20 | 50 | 109 | 137 | 173 | 101 | 29 | 0 |

| Example No. | 78 | 79 | 80 | 81 | 82 | 83 |
|---|---|---|---|---|---|---|
| Catalyst Components | DMF 3.0 mL POCl$_3$ 1.0 mL | DMF 3.0 mL POCl$_3$ 1.0 mL | DMF 3.0 mL POCl$_3$ 1.0 mL | DMF 3.0 mL POCl$_3$ 1.0 mL | DMF 3.0 mL POCl$_3$ 1.0 mL | DMF 3.0 mL POCl$_3$ 1.0 mL |
| Additives Charged with Oxime | SDS 11.0 g | SDS 10.0 g | (NH$_4$)$^+$(H$_2$PO$_4$)$^-$ 4.0 g | (NH$_4$)$^+$(H$_2$PO$_4$)$^-$ 4.0 g | Na Salt of Oxime 6.9 g CH$_3$SO$_3$H 2.92 mL | ArSO$_3$Na 7.9 g |
| Temp (°C.) | 50 | 50 | 50 | 50 | 50 | 50 |
| Time (min) | 19 | 18 | 60 | 60 | 17 | 60 |
| Oxime Conv (%) | 96.7 | 99.2 | 99.6 | 99.5 | 99.0 | 99.3 |
| Yields (%): | | | | | | |
| APAP | 88.7 | 90.3 | 96.3 | 93.6 | 98.6 | 103.3 |
| MHBA | 0.005 | 0.008 | 0.018 | 0.018 | 0.034 | 0.070 |
| Precipitated Solids: | | | | | | |
| Yield (%) | 77.2 | 78.9 | 90.2 | 86.2 | 90.6 | 93.9 |
| MHBA (ppm) | 6 | 10 | 37 | 38 | 101 | 97 |

TABLE 9

| Example No. | 84 | 85 | 86 | 87 |
|---|---|---|---|---|
| Catalyst Components | DMF 1.94 mL CCl$_3$COCl 2.23 mL | DMF 1.9 mL CCl$_3$COCl 2.2 g | DMF 3.0 mL CCl$_3$COCl 3.4 mL | DMF 1.9 mL ClCO$_2$CCl$_3$ 1.2 mL |
| Temp (°C.) | 50 | 70 | 70 | 50 |
| Time (min) | 36 | 30 | 60 | 60 |
| Oxime Conv (%) | 91.0 | 93.0 | 99.6 | 89.8 |
| Yields (%): | | | | |
| APAP | 85.0 | 86.0 | 95.3 | 91.7 |
| MHBA | 0.004 | 0.010 | 0.048 | 0.010 |
| Precipitated Solids: | | | | |
| Yield (%) | 70.5 | 71.6 | 85.5 | 92.0 |
| MHBA (ppm) | 10 | 31 | 90 | 69 |

TABLE 10

| Example No. | 88 | 89 | 90 | 91 | 92 | 93 | 94 | 95 | 96 | 97 | 98 |
|---|---|---|---|---|---|---|---|---|---|---|---|
| Catalyst Components | DMA 2.4 mL SOCl$_2$ 1.0 mL | DMA 3.3 mL SOCl$_2$ 1.4 mL | DMA 4.4 mL POCl$_3$ 1.2 mL | DMA 5.5 mL POCl$_3$ 1.5 mL | DMA 4.4 mL POCl$_3$ 1.2 mL | DMA 3.6 mL POCl$_3$ 1.0 mL | DMA 4.0 mL POCl$_3$ 1.1 mL | NMP 2.0 mL SOCl$_2$ 0.8 mL | NMP 2.0 mL POCl$_3$ 1.0 mL | NMP 2.4 mL POCl$_3$ 1.2 mL | NMP 2.4 mL POCl$_3$ 1.2 mL |
| Temp (°C.) | 50 | 50 | 25 | 50 | 50 | 50 | 50 | 50 | 50 | 25 | 25 |
| Time (min) | 60 | 18 | 112 | 30 | 18 | 60 | 60 | 60 | 60 | 60 | 60 |
| Oxime Conv (%) | 93.3 | 99.0 | 92.4 | 95.5 | 95.8 | 97.4 | 98.5 | 90.6 | 99.0 | 98.1 | 98.6 |
| Yields (%): | | | | | | | | | | | |
| APAP | 88.8 | 94.7 | 82.1 | 87.4 | 91.6 | 92.9 | 94.1 | 84.7 | 100.9 | 97.1 | 90.9 |
| MHBA | 0.010 | 0.032 | 0.005 | 0.018 | 0.009 | 0.015 | 0.032 | 0.018 | 0.066 | 0.010 | 0.020 |
| Precipitated Solids: | | | | | | | | | | | |
| Yield (%) | 81.6 | 86.3 | 72.1 | 78.0 | 83.9 | 84.6 | 85.9 | 76.2 | 86.1 | 85.9 | 78.7 |
| MHBA (ppm) | 29 | 106 | 0 | 77 | 28 | 37 | 76 | 150 | 137 | 15 | 71 |

TABLE 11

| Example No. | 99 | 100 | 101 | 102 | 103 | 104 | 105 |
|---|---|---|---|---|---|---|---|
| Catalyst Components | $SOCl_2$ 0.8 mL | $SOCl_2$ 1.0 mL | $SOCl_2$ 1.0 mL | $SOCl_2$ 1.4 mL | $SOCl_2$ 1.0 mL | $SOCl_2$ 0.8 mL | $SOCl_2$ 0.7 mL |
| Additives | | | | | | | |
| Charged with Oxime | $Na_2S_2O_5$ 1.6 g | $Na_2S_2O_5$ 6.0 g | $CH_3CO_2Na$ 1.6 g | $CF_3CO_2Na$ 5.4 g | $K_2SO_4$ 3.5 g | KI 1.0 g | $NEt_3$ 1.4 mL |
| Temp (°C.) | 50 | 50 | 50 | 50 | 50 | 50 | 53 |
| Time (min) | 54 | 60 | 30 | 90 | 36 | 60 | 47 |
| Oxime Conv (%) | 95.6 | 83.5 | 89.8 | 85.1 | 99.3 | 89.5 | 30.5 |
| Oxime Acct (%) | | | | | | | 92.7 |
| Efficiencies (%) to: | | | | | | | |
| APAP | | | | | | | 95.6 |
| MHBA | | | | | | | 0.000 |
| Yields (%): | | | | | | | |
| APAP | 90.3 | 68.1 | 85.3 | 61.6 | 103.0 | 79.1 | 27.0 |
| MHBA | 0.018 | 0 | 0.009 | 0 | 0.034 | 0.011 | 0.000 |
| Precipitated Solids: | | | | | | | |
| Yield (%) | 80.0 | 64.9 | 80.0 | 56.8 | 101.1 | 70.2 | 21.8 |
| MHBA (ppm) | 75 | 0 | 51 | 0 | 242 | 122 | 0 |

| Example No. | 106 | 107 | 108 | 109 | 110 | 111 | 112 |
|---|---|---|---|---|---|---|---|
| Catalyst Components | $SOCl_2$ 0.8 mL $SO_2$ | $SOCl_2$ 1.1 mL $SO_2$ 12.1 g (sparged separately) | $SOCl_2$ 1.1 mL $SO_2$ 9.9 g (sparged separately) | $SOCl_2$ 1.1 mL | $SOCl_2$ 1.0 mL | $SOCl_2$ 0.8 mL | $SOCl_2$ 1.1 mL |
| Additives | | | | | | | |
| Charged with Oxime | | | | $B(OCH_3)_3$ 3.4 mL | SDS 10.0 g | CTMAB 2.5 g | $HCO_2H$ 2.0 mL |
| Temp (°C.) | 50 | 50 | 50 | 50 | 50 | 50 | 50 |
| Time (min) | 60 | 60 | 60 | 60 | 60 | 67 | 90 |
| Oxime Conv (%) | 91.0 | 94.3 | 98.6 | 98.4 | 83.6 | 99.4 | 80.5 |
| Oxime Acct (%) | | | | | | | |
| Efficiencies (%) to: | | | | | | | |
| APAP | | | | | | | |
| MHBA | | | | | | | |
| Yields (%): | | | | | | | |
| APAP | 79.6 | 89.6 | 98.1 | 99.1 | 94.9 | 95.2 | 38.4 |
| MHBA | 0.012 | 0.022 | 0.047 | 0.027 | 0.004 | 0.051 | 0 |
| Precipitated Solids: | | | | | | | |
| Yield (%) | 71.0 | 90.2 | 96.4 | 98.4 | 84.8 | 87.6 | 31.8 |
| MHBA (ppm) | 36 | 138 | 372 | 160 | 17 | 233 | 0 |

TABLE 12

| Example No. | 113 | 114 | 115 | 116 | 117 | 118 |
|---|---|---|---|---|---|---|
| Oximation Reflux Period (min) | 45 | 45 | 45 | 60 | 60 | 60 |
| Ethyl Acetate Used to Extract Oxime: | | | | | | |
| Source | Previous Batch | Example 113 | Example 114 | Fresh | Example 116 | Example 117 |
| Amount (g) | 226 | 223 | 226 | 270 | 287 | 318 |
| Ethyl Acetate Added to Oxime Extract: | | | | | | |
| Before Azeo Drying with Dean Stark Trap: | | | | | | |
| Source | Previous Batch | Example 113 | Example 114 | | Example 116 | Example 117 |
| Amount (g) | 173.61 | 151.40 | 123.0 | 0 | 260.0 | 284.0 |
| Solutes (Wt %): | | | | | | |
| APAP | 4.85 | 4.90 | 5.17 | | 7.90 | 8.40 |
| 4-HAP Oxime | 4.28 | 4.96 | 4.15 | | 5.20 | 6.30 |
| 4-HAP | 2.11 | 2.84 | 2.95 | | 0.49 | 0.86 |
| All Others (Total) | 0.26 | 0.28 | 0.35 | | 0.13 | 0.23 |
| After Azeo Drying with Dean Stark Trap: | | | | | | |
| Amount (g) | 45.0 | 108.0 | 135.0 | 225.0 | 90.0 | 90.0 |
| Azeotropic Drying: | | | | | | |
| Water (g) Removed in Dean Stark Trap | 51.7 | 48.32 | 46.82 | 39.42 | 54.66 | 61.35 |
| Oldershaw Distillation: | | | | | | |
| Reflux:Takeoff Ratio | 3:1 | 3:1 | 3:1 | 1:1 | 1:1 | 1:1 |
| Distillate Takeoff (mL) | 240 | 243 | 220 | 310 | 400 | 440 |
| Vilsmeier Reagent Catalyst for Beckmann Reaction: | | | | | | |

TABLE 12-continued

| Example No. | 113 | 114 | 115 | 116 | 117 | 118 |
|---|---|---|---|---|---|---|
| $SOCl_2$ (mL) | 1.3 | 1.3 | 1.3 | 0.8 | 1.0 | 1.1 |
| DMF (mL) | 2.3 | 2.3 | 2.3 | 1.3 | 1.7 | 1.9 |
| Ethyl Acetate (mL) | 30 | 30 | 30 | 15 | 20 | 20 |
| Oxime Conversion (%) | 90.246 | 93.352 | 88.529 | 83.055 | 79.392 | 76.340 |
| Efficiencies (%) to: | | | | | | |
| APAP | 96.495 | 97.942 | 96.539 | 96.041 | 96.018 | 95.383 |
| 4-HAP | 3.471 | 1.905 | 3.227 | 3.485 | 3.510 | 3.906 |
| MHBA | 0.000 | 0.003 | 0.004 | 0.008 | 0.000 | 0.001 |
| All Others (Total) | 0.034 | 0.150 | 0.230 | 0.466 | 0.472 | 0.710 |
| Accountability (%) of all aromatic feed (recycled plus fresh) | 87.236 | 85.813 | 83.958 | 77.332 | 80.369 | 81.114 |
| Purified APAP: | | | | | | |
| Impurities Detectable by HPLC, Total Wt % | <0.10 | <0.10 | <0.10 | <0.10 | <0.10 | <0.10 |
| MHBA Content (ppm) | 0 | 0 | 9 | 0 | 0 | 0 |
| Limit of Color | 0.017 | 0.011 | 0.011 | 0.007 | 0.008 | 0.012 |
| Melting Point (°C.) | 169–170 | 169–170 | 169–170 | 169–170 | 169–170 | 169–170 |
| As a Molar Percentage of all Unrecycled Output: | | | | | | |
| Purified APAP | 87.729 | 88.842 | 88.899 | 80.717 | 86.174 | 83.185 |
| Total Aromatics in Waste Streams | 12.271 | 11.158 | 11.101 | 19.283 | 13.826 | 16.815 |
| Total Yield (% based on Fresh 4-HAP Feed) of all Aromatics in all Unrecycled Output | 84.268 | 86.520 | 72.828 | 40.547 | 64.713 | 70.146 |
| Ethyl Acetate Filtrate from Present Beckmann Reaction: | | | | | | |
| Amount (g) | 151.92 | 123.72 | 238.43 | 261.49 | 285.12 | 254.98 |
| Solutes (Wt %): | | | | | | |
| APAP | 4.90 | 5.17 | 4.00 | 7.90 | 8.40 | 8.38 |
| 4-HAP Oxime | 4.96 | 4.15 | 4.00 | 5.20 | 6.30 | 7.44 |
| 4-HAP | 2.84 | 2.95 | 2.00 | 0.49 | 0.86 | 1.35 |
| All Others (Total) | 0.28 | 0.35 | 0.24 | 0.13 | 0.23 | 0.45 |

TABLE 13

| Example No. | 119 | 120 | 121 | 122 | 123 |
|---|---|---|---|---|---|
| Oxime Conversion (%) | 87.006 | 84.729 | 87.231 | 98.196 | 99.690 |
| Efficiencies (%) to: | | | | | |
| APAP | 92.324 | 92.642 | 98.705 | 98.775 | 98.453 |
| 4-HAP | 7.232 | 7.217 | 1.216 | 0.908 | 0.711 |
| MHBA | 0.012 | 0.011 | 0.013 | 0.000 | 0.006 |
| All Others (Total) | 0.432 | 0.130 | 0.066 | 0.317 | 0.830 |
| Accountability (%) of all aromatic feed (recycled plus fresh) | 81.358 | 83.468 | 91.859 | 97.245 | 98.884 |
| Purified APAP: | | | | | |
| Impurities Detectable by HPLC, Total Wt % | <0.10 | <0.10 | <0.10 | <0.10 | <0.80 |
| MHBA Content (ppm) | 7 | 7 | 7 | 0 | 25 |
| Melting Point (°C.) | | | | 169–170 | |
| As a Molar Percentage of all Unrecycled Output: | | | | | |
| Purified APAP | 86.565 | 86.098 | 90.901 | 90.112 | 89.538 |
| Total Aromatics in Waste Streams | 13.435 | 13.902 | 9.099 | 9.888 | 10.462 |
| Total Yield (% based on Fresh Feed) of all Aromatics in all Unrecycled Output | 81.445 | 71.732 | 92.996 | 97.245 | 98.884 |
| n-Butyl Acetate Beckmann Reaction Filtrate Added to n-Butyl Acetate Extract of Oxime: | | | | | |
| Source: | Previous Batch | Example 119 | Example 120 | | |
| Amount (g) | 2240 | 3000 | 3360 | | |
| Solutes (Wt %): | | | | | |
| APAP | 3.28 | 2.2 | 2.3 | | |
| 4-HAP Oxime | 10.13 | 4.1 | 4.0 | | |
| 4-HAP | 2.85 | 3.2 | 3.2 | | |
| All Others (Total) | 0.24 | 0.3 | 0.2 | | |
| n-Butyl Acetate Filtrate from Present Beckmann Reaction: | | | | | |
| Amount (g) | 3000 | 3371 | 3058 | | |
| Solutes (Wt %): | | | | | |
| APAP | 2.2 | 2.3 | 2.5 | | |
| 4-HAP Oxime | 4.1 | 4.0 | 4.2 | | |
| 4-HAP | 3.2 | 3.2 | 3.5 | | |
| All Others (Total) | 0.3 | 0.2 | 0.2 | | |

What is claimed is:

1. A process for production of N-acetyl-para-aminophenol from 4-hydroxyacetophenone oxime comprising adding a Beckmann rearrangement catalyst to said 4-hydroxyacetophenone oxime to form said N-acetyl-para-aminophenol product, said catalyst having an electrophilic carbon atom at which said catalyst reacts with said oxime.

2. The process of claim 1, wherein said Beckmann rearrangement catalyst comprises a nitrilium cation.

3. The process of claim 2, wherein said nitrilium cation is N-methylacetonitrilium cation.

4. The process of claim 2, wherein said Beckmann rearrangement catalyst further comprises tetrafluoroborate anion.

5. The process of claim 4, wherein said Beckmann rearrangement catalyst is N-methylacetonitrilium tetrafluoroborate.

6. The process of claim 1, wherein said Beckmann rearrangement catalyst is a trihaloacetic anhydride.

7. The process of claim 1, wherein said Beckmann rearrangement catalyst is a Vilsmeier reagent prepared from a carboxylic acid amide.

8. The process of claim 7, wherein said amide is N,N-dimethylformamide.

9. The process of claim 1, wherein the Beckmann rearrangement is conducted in an alkyl alkanoate solvent.

10. The process of claim 9, wherein the amount of said Beckmann rearrangement catalyst is selected to achieve a conversion of said 4-hydroxyacetophenone oxime in the range of 50% to 95% to lessen formation of N-methyl-p-hydroxybenzamide.

11. The process of claim 9, wherein said 4-hydroxyacetophenone oxime is reacted in the presence of a base to lessen formation of N-methyl-p-hydroxybenzamide.

12. The process of claim 11 wherein said base is a metabisulfite salt.

13. The process of claim 11 wherein said base is a salt of a carboxylic acid.

14. The process of claim 11 wherein said base is a tertiary amine.

15. The process of claim 11 wherein said base is a phosphate salt.

16. A process for production of N-acetyl-para-aminophenol from 4-hydroxyacetophenone oxime comprising contacting a mixture of an alkyl alkanoate solvent and said 4-hydroxyacetophenone oxime with an amount of a Beckmann rearrangement catalyst selected to achieve a conversion of said 4-hydroxyacetophenone oxime to said N-acetyl-para-aminophenol in the range of about 50% to about 95% to reduce formation of N-methyl-p-hydroxybenzamide.

17. A process for production of N-acetyl-para-aminophenol from 4-hydroxyacetophenone oxime comprising contacting a mixture of an alkyl alkanoate solvent and said 4-hydroxyacetophenone oxime with activated carbon to remove colored impurities and contacting said mixture with a Beckmann rearrangement catalyst to produce said N-acetyl-para-aminophenol.

18. The process of claim 17 wherein said activated carbon is removed prior to contacting said mixture with the Beckmann rearrangement catalyst.

19. A process for production of N-acetyl-para-aminophenol from 4-hydroxyacetophenone oxime comprising contacting a mixture of said 4-hydroxyacetophenone oxime and a substantially water-immiscible solvent with a Beckmann rearrangement catalyst to form a first product mixture of said N-acetyl-para-aminophenol and said solvent, adding water to said first product mixture and forming a second product mixture of said N-acetyl-para-aminophenol, said water and said substantially water-immiscible solvent, and subsequently removing substantially all of said substantially water-immiscible solvent from said second product mixture.

20. The process of claim 19 wherein said second product mixture comprises solid N-acetyl-para-aminophenol.

21. The process of claim 20 wherein said first product mixture comprises solid N-acetyl-para-aminophenol, the process further comprising, removing a portion of said solvent from said first product mixture by filtration.

22. The process of claim 21 further comprising: washing said first product mixture with said substantially water-immiscible solvent and recovering from said washing a wash liquor of recyclable aromatics in said substantially water-immiscible solvent.

23. The process of claim 21, wherein said removal of substantially all of said substantially water-immiscible solvent from said second product mixture is achieved by washing said second product mixture with an aqueous medium.

24. The process of claim 23 further comprising recovering an aqueous wash liquor from said washing of said second product mixture and extracting said aqueous wash liquor with said substantially water-immiscible solvent to obtain a solution of recyclable aromatics in said substantially water-immiscible solvent.

25. The process of claim 24 wherein said aqueous wash liquor is extracted with at least a portion of said solvent removed from said first product mixture by filtration.

26. The process of claim 19, wherein said removal of said substantially water-immiscible solvent from said second product mixture is achieved by distillation.

27. The process of claim 26, wherein substantially all of said solvent in said first product mixture is contained in said second product mixture and wherein said process comprises removing substantially all of said substantially water-immiscible solvent from said second product mixture by distillation.

28. The process of claim 26, wherein said distillation is carried out by passing water vapor into said second product mixture.

29. The process of claim 26 wherein said second product mixture comprises solid N-acetyl-para-aminophenol.

30. The process of claim 29, wherein said first product mixture comprises solid N-acetyl-para-aminophenol, said process comprising, removing a portion of said solvent from said first product mixture by filtration.

31. A process for production of N-acetyl-para-aminophenol from 4-hydroxyacetophenone comprising reacting said 4-hydroxyacetophenone with hydroxylamine in the presence of water to form 4-hydroxyacetophenone oxime, extracting said oxime with a substantially water-immiscible solvent to form an aqueous first mixture and a second mixture of said oxime in said substantially water-immiscible solvent, contacting said second mixture with a Beckmann rearrangement catalyst to form a first product mixture of said N-acetyl-para-aminophenol and said solvent, adding water to said first product mixture and forming a second product mixture of said N-acetyl-para-aminophenol, said water and said water-immiscible solvent, and subsequently removing substantially all of said substantially water-immiscible solvent from said second product mixture.

32. The process of claim 31 wherein said second product mixture comprises solid N-acetyl-para-aminophenol and wherein said removal of substantially all of said substantially water-immiscible solvent from said second product mixture is achieved by washing said second product mixture comprising said solid N-acetyl-para-aminophenol with an aqueous medium.

33. The process of claim 32, wherein said aqueous medium comprises at least a portion of said first mixture.

34. The process of claim 32 further comprising recovering an aqueous wash liquor from said washing of said second product mixture and extracting said aqueous wash liquor with said substantially water-immiscible solvent to obtain a solution of recyclable aromatics in said substantially water-immiscible solvent.

35. The process of claim 32 wherein said first product mixture contains solid N-acetyl-para-aminophenol, said process further comprising removing a portion of said solvent from said first product mixture by filtration and extracting said first mixture with at least a portion of said solvent removed from said first product mixture by filtration.

36. The process of claim 31, wherein said oxime is formed by contacting said 4-hydroxyacetophenone with a hydroxyl amine salt and an alkali metal hydroxide.

37. A process for production of N-acetyl-para-aminophenol from 4-hydroxyacetophenone oxime comprising contacting said 4-hydroxyacetophenone oxime in an alkyl alkanoate solvent with both a Beckmann rearrangement catalyst to form said n-acetyl-para-aminophenol product and a base to reduce formation of N-methyl-p-hydroxy benzamide.

38. The process of claim 37 wherein said base is a metabisulfite salt.

39. The process of claim 37 wherein said base is a salt of a carboxylic acid.

40. The process of claim 37 wherein said base is a tertiary amine.

41. The process of claim 37 wherein said base is a phosphate salt.

* * * * *